United States Patent [19]
Kubota et al.

[11] Patent Number: 5,871,977
[45] Date of Patent: Feb. 16, 1999

[54] DNA ENCODING ENZYME RECOMBINANT DNA AND ENZYME TRANSFORMANT, AND THEIR PREPARATION AND USES

[75] Inventors: Michio Kubota, Osaka; Keiji Tsusaki, Okayama; Kazuhiko Maruta, Okayama; Toshiyuki Sugimoto, Okayama, all of Japan

[73] Assignee: Kabushiki Kaisha Hayashibara Seibutsu Kagaku Kenkyujo, Okayama, Japan

[21] Appl. No.: 714,677

[22] Filed: Sep. 16, 1996

Related U.S. Application Data

[62] Division of Ser. No. 393,540, Feb. 23, 1995.

[30] Foreign Application Priority Data

| Feb. 23, 1994 | [JP] | Japan | 6-47940 |
| Feb. 23, 1994 | [JP] | Japan | 6-47956 |
| Apr. 6, 1994 | [JP] | Japan | 6-90705 |
| Apr. 6, 1994 | [JP] | Japan | 6-90728 |

[51] Int. Cl.$^6$ .............. C12P 19/12; C12N 9/24; C12N 1/21; C07H 21/04
[52] U.S. Cl. .......... 435/100; 435/101; 435/200; 435/320.1; 435/252.3; 536/23.2
[58] Field of Search ............... 435/100, 101, 435/200, 201, 320.1, 252.3; 536/23.2

[56] References Cited

U.S. PATENT DOCUMENTS

| 4,521,252 | 6/1985 | Miyake et al. | 127/46.3 |
| 5,455,168 | 10/1995 | Maruta et al. | 435/201 |
| 5,484,714 | 1/1996 | Tsuchida et al. | 435/100 |

FOREIGN PATENT DOCUMENTS

| 0555540A1 | 8/1993 | European Pat. Off. . |
| 0606753A3 | 7/1994 | European Pat. Off. . |
| 154485 | 12/1975 | Japan . |
| 2379983 | 2/1983 | Japan . |
| 7259883 | 4/1983 | Japan . |
| 216695 | 12/1983 | Japan . |
| 2106912 | 4/1983 | United Kingdom . |

OTHER PUBLICATIONS

U.K. Laemmli, "Cleavage of Structural Proteins During the Assembly of the Head of Bacteriophage T4", Nature, vol. 227, pp. 680–685, Aug. 15, 1970.

Sambrook et al, Molecular Cloning, A Laboratory Manual, Second Edition, Cold Springs Harbor Press, 1989.

E.M. Southern, "Detection of Specific Sequences Among DNA Fragments Separated by Gel Electrophoresis", J. Mol. Biol., vol. 98, pp. 503–517, 1975.

*Primary Examiner*—Kawai Lau
*Attorney, Agent, or Firm*—Browdy and Neimark

[57] ABSTRACT

A DNA encoding an enzyme, which forms non-reducing saccharides having trehalose structure as an end unit from amylaceous saccharides having a degree of glucose polymerization of 3 or higher, enables an industrial-scale production of a recombinant enzyme with such enzyme activity. Non-reducing saccharides obtainable by the recombinant enzyme can be used in a variety of food products, cosmetics, pharmaceuticals and feeds because of their substantial non-reducibility, mild and high-quality sweetness, adequate viscosity, and moisture-retaining ability.

12 Claims, 10 Drawing Sheets

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 2316 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..2316

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | AGG | ACA | CCC | GCC | TCG | ACC | TAC | CGG | CTG | CAG | ATC | AGG | CGG | GGT | TTC | 48 |
| Met | Arg | Thr | Pro | Ala | Ser | Thr | Tyr | Arg | Leu | Gln | Ile | Arg | Arg | Gly | Phe | |
| 1 | | | | 5 | | | | | 10 | | | | | 15 | | |
| ACG | CTG | TTT | GAT | GCC | GCC | GAG | ACC | GTG | CCC | TAC | CTG | AAG | TCA | CTC | GGG | 96 |
| Thr | Leu | Phe | Asp | Ala | Ala | Glu | Thr | Val | Pro | Tyr | Leu | Lys | Ser | Leu | Gly | |
| | | | 20 | | | | | 25 | | | | | 30 | | | |
| GTG | GAC | TGG | ATC | TAC | CTG | TCG | CCC | ATC | CTG | AAG | GCA | GAG | AGC | GGC | TCC | 144 |
| Val | Asp | Trp | Ile | Tyr | Leu | Ser | Pro | Ile | Leu | Lys | Ala | Glu | Ser | Gly | Ser | |
| | | 35 | | | | | 40 | | | | | 45 | | | | |
| GAC | CAC | GGC | TAT | GAC | GTC | ACC | GAT | CCC | GCC | GTA | GTG | GAC | CCG | GAG | CGC | 192 |
| Asp | His | Gly | Tyr | Asp | Val | Thr | Asp | Pro | Ala | Val | Val | Asp | Pro | Glu | Arg | |
| | 50 | | | | | 55 | | | | | 60 | | | | | |
| GGC | GGC | CCT | GAA | GGG | CTG | GCC | GCG | GTG | TCC | AAG | GCG | GCC | CGC | GGT | GCC | 240 |
| Gly | Gly | Pro | Glu | Gly | Leu | Ala | Ala | Val | Ser | Lys | Ala | Ala | Arg | Gly | Ala | |
| 65 | | | | | 70 | | | | | 75 | | | | | 80 | |
| GGC | ATG | GGC | GTG | CTG | ATC | GAC | ATC | GTG | CCG | AAC | CAC | GTG | GGC | GTG | GCG | 288 |
| Gly | Met | Gly | Val | Leu | Ile | Asp | Ile | Val | Pro | Asn | His | Val | Gly | Val | Ala | |
| | | | | 85 | | | | | 90 | | | | | 95 | | |
| TCG | CCG | CCG | CAG | AAC | CCG | TGG | TGG | TGG | TCG | CTG | CTC | AAG | GAA | GGG | CGC | 336 |
| Ser | Pro | Pro | Gln | Asn | Pro | Trp | Trp | Trp | Ser | Leu | Leu | Lys | Glu | Gly | Arg | |
| | | | 100 | | | | | 105 | | | | | 110 | | | |
| GGG | TCG | CCC | TAC | GCC | GTG | GCG | TTC | GAC | GTC | GAC | TGG | GAC | CTG | GCG | GGG | 384 |
| Gly | Ser | Pro | Tyr | Ala | Val | Ala | Phe | Asp | Val | Asp | Trp | Asp | Leu | Ala | Gly | |
| | | 115 | | | | | 120 | | | | | 125 | | | | |
| GGC | CGC | ATC | CGG | ATC | CCC | GTC | CTG | GGC | AGC | GAC | GAC | GAT | CTG | GAC | CAG | 432 |
| Gly | Arg | Ile | Arg | Ile | Pro | Val | Leu | Gly | Ser | Asp | Asp | Asp | Leu | Asp | Gln | |
| | 130 | | | | | 135 | | | | | 140 | | | | | |
| CTC | GAA | ATC | AAG | GAC | GGC | GAG | CTG | CGG | TAC | TAC | GAC | CAC | CGC | TTC | CCG | 480 |
| Leu | Glu | Ile | Lys | Asp | Gly | Glu | Leu | Arg | Tyr | Tyr | Asp | His | Arg | Phe | Pro | |
| 145 | | | | | 150 | | | | | 155 | | | | | 160 | |
| CTG | GCC | GAG | GGC | AGC | TAC | CGG | GAC | GGC | GAC | TCC | CCG | CAG | GAC | GTC | CAC | 528 |
| Leu | Ala | Glu | Gly | Ser | Tyr | Arg | Asp | Gly | Asp | Ser | Pro | Gln | Asp | Val | His | |
| | | | | 165 | | | | | 170 | | | | | 175 | | |
| GGC | CGG | CAG | CAC | TAC | GAA | CTC | ATC | GGC | TGG | CGG | CGC | GCC | GAC | AAT | GAA | 576 |
| Gly | Arg | Gln | His | Tyr | Glu | Leu | Ile | Gly | Trp | Arg | Arg | Ala | Asp | Asn | Glu | |
| | | | 180 | | | | | 185 | | | | | 190 | | | |
| CTG | AAC | TAC | CGC | CGG | TTC | TTC | GCG | GTG | AAC | ACG | CTC | GCC | GGC | ATC | CGG | 624 |
| Leu | Asn | Tyr | Arg | Arg | Phe | Phe | Ala | Val | Asn | Thr | Leu | Ala | Gly | Ile | Arg | |
| | | 195 | | | | | 200 | | | | | 205 | | | | |
| GTG | GAG | GTG | CCG | CCG | GTC | TTC | GAT | GAA | GCG | CAC | CAG | GAG | GTG | GTG | CGC | 672 |
| Val | Glu | Val | Pro | Pro | Val | Phe | Asp | Glu | Ala | His | Gln | Glu | Val | Val | Arg | |
| | 210 | | | | | 215 | | | | | 220 | | | | | |
| TGG | TTC | CGT | GCG | GGG | CTC | GCC | GAC | GGG | CTG | CGG | ATC | GAC | CAC | CCG | GAC | 720 |
| Trp | Phe | Arg | Ala | Gly | Leu | Ala | Asp | Gly | Leu | Arg | Ile | Asp | His | Pro | Asp | |
| 225 | | | | | 230 | | | | | 235 | | | | | 240 | |
| GGC | CTG | GCC | GAT | CCC | GAG | GGG | TAT | TTG | AAG | CGG | CTC | CGT | GAG | GTC | ACC | 768 |
| Gly | Leu | Ala | Asp | Pro | Glu | Gly | Tyr | Leu | Lys | Arg | Leu | Arg | Glu | Val | Thr | |
| | | | | 245 | | | | | 250 | | | | | 255 | | |
| GGG | GGC | GCG | TAC | CTG | CTC | ATC | GAA | AAG | ATC | CTC | GAG | CCG | GGC | GAA | CAG | 816 |
| Gly | Gly | Ala | Tyr | Leu | Leu | Ile | Glu | Lys | Ile | Leu | Glu | Pro | Gly | Glu | Gln | |
| | | | 260 | | | | | 265 | | | | | 270 | | | |
| TTG | CCG | GCC | AGC | TTC | GAG | TGC | GAA | GGC | ACC | ACC | GGC | TAC | GAC | GCC | CTC | 864 |
| Leu | Pro | Ala | Ser | Phe | Glu | Cys | Glu | Gly | Thr | Thr | Gly | Tyr | Asp | Ala | Leu | |
| | | 275 | | | | | 280 | | | | | 285 | | | | |
| GCG | GAT | GTC | GAC | AGG | GTC | TTC | GTG | GAC | CCG | CGG | GGA | CAG | GTG | CCG | CTG | 912 |
| Ala | Asp | Val | Asp | Arg | Val | Phe | Val | Asp | Pro | Arg | Gly | Gln | Val | Pro | Leu | |
| | 290 | | | | | 295 | | | | | 300 | | | | | |
| GAC | CGT | CTG | GAC | GCA | CGG | CTG | CGC | GGC | GGT | GCG | CCG | GCC | GAC | TAC | GAG | 960 |
| Asp | Arg | Leu | Asp | Ala | Arg | Leu | Arg | Gly | Gly | Ala | Pro | Ala | Asp | Tyr | Glu | |
| 305 | | | | | 310 | | | | | 315 | | | | | 320 | |

```
GAC ATG ATC CGC GGG ACC AAG CGC CGG ATC ACC GAC GGC ATC CTG CAC   1008
Asp Met Ile Arg Gly Thr Lys Arg Arg Ile Thr Asp Gly Ile Leu His
            325                     330                 335

TCC GAG ATC CTG CGC CTT GCC AGG CTG GTG CCC GAG CAG ACC GGA ATT   1056
Ser Glu Ile Leu Arg Leu Ala Arg Leu Val Pro Glu Gln Thr Gly Ile
        340                     345                 350

CCC GGG GAG GCG GCC GCG GAT GCG ATC GCG GAG ATC ATC GCG GCC TTC   1104
Pro Gly Glu Ala Ala Ala Asp Ala Ile Ala Glu Ile Ile Ala Ala Phe
            355                     360                 365

CCG GTC TAC CGG TCC TAT CTT CCC GAG GGC GCG GAG ATC CTG AAG GAG   1152
Pro Val Tyr Arg Ser Tyr Leu Pro Glu Gly Ala Glu Ile Leu Lys Glu
        370                     375                 380

GCC TGC GAC CTC GCC GCG CGG AGG CGT CCG GAA CTG GGC CAG ACC GTC   1200
Ala Cys Asp Leu Ala Ala Arg Arg Arg Pro Glu Leu Gly Gln Thr Val
385                     390                     395             400

CAG CTG CTG CAG CCG CTG CTG CTG GAT ACC GAC CTC GAG ATT TCC CGC   1248
Gln Leu Leu Gln Pro Leu Leu Leu Asp Thr Asp Leu Glu Ile Ser Arg
                405                     410                 415

AGG TTC CAG CAG ACC TCG GGA ATG GTC ATG GCC AAA GGC GTG GAG GAC   1296
Arg Phe Gln Gln Thr Ser Gly Met Val Met Ala Lys Gly Val Glu Asp
            420                     425                 430

ACC GCG TTC TTC CGC TAC AAC CGG CTG GGA ACG CTC ACC GAG GTG GGC   1344
Thr Ala Phe Phe Arg Tyr Asn Arg Leu Gly Thr Leu Thr Glu Val Gly
        435                     440                 445

GCC GAC CCC ACC GAG TTC TCG CTG GAA CCG GAG GAG TTT CAC GTC CGG   1392
Ala Asp Pro Thr Glu Phe Ser Leu Glu Pro Glu Glu Phe His Val Arg
        450                     455                 460

ATG GCC CGC CGG CAG GCC GAA CTC CCG CTC TCC ATG ACC ACC CTG AGC   1440
Met Ala Arg Arg Gln Ala Glu Leu Pro Leu Ser Met Thr Thr Leu Ser
465                     470                     475             480

ACG CAC GAC ACC AAG CGC AGC GAG GAC ACC CGG GCC CGG ATC TCG GTG   1488
Thr His Asp Thr Lys Arg Ser Glu Asp Thr Arg Ala Arg Ile Ser Val
                485                     490                 495

ATC GCC GAG GTC GCG CCT GAA TGG GAA AAG GCC CTG GAC AGG CTG AAC   1536
Ile Ala Glu Val Ala Pro Glu Trp Glu Lys Ala Leu Asp Arg Leu Asn
            500                     505                 510

ACC CTC GCT CCG CTG CCG GAC GGC CCG CTC TCC ACG CTG CTC TGG CAG   1584
Thr Leu Ala Pro Leu Pro Asp Gly Pro Leu Ser Thr Leu Leu Trp Gln
        515                     520                 525

GCG ATT GCG GGG GCA TGG CCG GCC AGC CGG GAA CGC CTT CAG TCC TAC   1632
Ala Ile Ala Gly Ala Trp Pro Ala Ser Arg Glu Arg Leu Gln Ser Tyr
        530                     535                 540

GCC CTG AAA GCG GCG CGC GAA GCC GGG AAC TCG ACC AGC TGG ACC GAT   1680
Ala Leu Lys Ala Ala Arg Glu Ala Gly Asn Ser Thr Ser Trp Thr Asp
545                     550                     555             560

CCG GAC CCG GCA TTC GAG GAG GCA CTT TCC GCC GTC GTC GAC TCC GCC   1728
Pro Asp Pro Ala Phe Glu Glu Ala Leu Ser Ala Val Val Asp Ser Ala
                565                     570                 575

TTC GAC AAT CCG GAG GTG CGT GCG GAA CTT GAG GCC CTG GTG GGC CTC   1776
Phe Asp Asn Pro Glu Val Arg Ala Glu Leu Glu Ala Leu Val Gly Leu
            580                     585                 590

CTT GCG CCG CAC GGT GCG TCC AAC TCG CTC GCG GCA AAG CTT GTC CAG   1824
Leu Ala Pro His Gly Ala Ser Asn Ser Leu Ala Ala Lys Leu Val Gln
        595                     600                 605

CTG ACC ATG CCG GGC GTT CCG GAC GTG TAC CAG GGC ACC GAG TTC TGG   1872
Leu Thr Met Pro Gly Val Pro Asp Val Tyr Gln Gly Thr Glu Phe Trp
        610                     615                 620

GAC AGG TCG CTG ACC GAT CCG GAC AAC CGG CGC CCC TTC AGC TTC GCC   1920
Asp Arg Ser Leu Thr Asp Pro Asp Asn Arg Arg Pro Phe Ser Phe Ala
625                     630                     635             640
```

```
GAA  CGG  ATT  AGG  GCC  TTG  GAC  CAG  TTG  GAC  GCC  GGC  CAC  CGT  CCG  GAC    1968
Glu  Arg  Ile  Arg  Ala  Leu  Asp  Gln  Leu  Asp  Ala  Gly  His  Arg  Pro  Asp
          645                      650                      655

TCC  TTC  CAG  GAC  GAG  GCG  GTC  AAG  CTG  CTG  GTC  ACC  TCG  AGG  GCG  CTG    2016
Ser  Phe  Gln  Asp  Glu  Ala  Val  Lys  Leu  Leu  Val  Thr  Ser  Arg  Ala  Leu
          660                      665                      670

CGG  CTG  CGG  CGG  AAC  CGG  CCC  GAG  CTC  TTC  ACC  GGC  TAC  CGC  CCC  GTG    2064
Arg  Leu  Arg  Arg  Asn  Arg  Pro  Glu  Leu  Phe  Thr  Gly  Tyr  Arg  Pro  Val
          675                      680                      685

CAT  GCC  AGG  GGC  CCC  GCC  GCC  GGG  CAC  CTG  GTG  GCG  TTC  GAC  CGC  GGC    2112
His  Ala  Arg  Gly  Pro  Ala  Ala  Gly  His  Leu  Val  Ala  Phe  Asp  Arg  Gly
          690                      695                      700

GCC  GGG  GGA  GTG  CTG  GCG  CTT  GCC  ACC  CGG  CTC  CCC  TAC  GGG  CTG  GAA    2160
Ala  Gly  Gly  Val  Leu  Ala  Leu  Ala  Thr  Arg  Leu  Pro  Tyr  Gly  Leu  Glu
705                      710                      715                      720

CAG  TCG  GGC  GGC  TGG  CGG  GAC  ACC  GCC  GTC  GAG  CTT  GAA  GCC  GCC  ATG    2208
Gln  Ser  Gly  Gly  Trp  Arg  Asp  Thr  Ala  Val  Glu  Leu  Glu  Ala  Ala  Met
          725                      730                      735

ACG  GAC  GAA  CTG  ACC  GGC  TCC  ACT  TTC  GGG  CCG  GGA  CCG  GCG  GCG  CTG    2256
Thr  Asp  Glu  Leu  Thr  Gly  Ser  Thr  Phe  Gly  Pro  Gly  Pro  Ala  Ala  Leu
          740                      745                      750

TCA  GAA  GTC  TTC  CGG  GCC  TAC  CCG  GTG  GCC  TTG  TTG  GTC  CCC  GCG  ACA    2304
Ser  Glu  Val  Phe  Arg  Ala  Tyr  Pro  Val  Ala  Leu  Leu  Val  Pro  Ala  Thr
          755                      760                      765

GGA  GGC  AAG  TCA                                                                2316
Gly  Gly  Lys  Ser
          770
```

( 2 ) INFORMATION FOR SEQ ID NO:2:

( i ) SEQUENCE CHARACTERISTICS:
        ( A ) LENGTH: 772 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Thr  Pro  Ala  Ser  Thr  Tyr  Arg  Leu  Gln  Ile  Arg  Arg  Gly  Phe
1                   5                        10                      15

Thr  Leu  Phe  Asp  Ala  Ala  Glu  Thr  Val  Pro  Tyr  Leu  Lys  Ser  Leu  Gly
               20                      25                      30

Val  Asp  Trp  Ile  Tyr  Leu  Ser  Pro  Ile  Leu  Lys  Ala  Glu  Ser  Gly  Ser
               35                      40                      45

Asp  His  Gly  Tyr  Asp  Val  Thr  Asp  Pro  Ala  Val  Val  Asp  Pro  Glu  Arg
          50                      55                      60

Gly  Gly  Pro  Glu  Gly  Leu  Ala  Ala  Val  Ser  Lys  Ala  Ala  Arg  Gly  Ala
65                       70                      75                       80

Gly  Met  Gly  Val  Leu  Ile  Asp  Ile  Val  Pro  Asn  His  Val  Gly  Val  Ala
                    85                      90                      95

Ser  Pro  Pro  Gln  Asn  Pro  Trp  Trp  Ser  Leu  Leu  Lys  Glu  Gly  Arg
                    100                     105                     110

Gly  Ser  Pro  Tyr  Ala  Val  Ala  Phe  Asp  Val  Asp  Trp  Asp  Leu  Ala  Gly
               115                     120                     125

Gly  Arg  Ile  Arg  Ile  Pro  Val  Leu  Gly  Ser  Asp  Asp  Leu  Asp  Gln
          130                     135                     140

Leu  Glu  Ile  Lys  Asp  Gly  Glu  Leu  Arg  Tyr  Tyr  Asp  His  Arg  Phe  Pro
145                      150                     155                     160

Leu  Ala  Glu  Gly  Ser  Tyr  Arg  Asp  Gly  Asp  Ser  Pro  Gln  Asp  Val  His
```

|     |     |     |     | 165 |     |     |     | 170 |     |     |     | 175 |     |     |
| --- | --- | --- | --- | --- | --- | --- | --- | --- | --- | --- | --- | --- | --- | --- |
| Gly | Arg | Gln | His<br>180 | Tyr | Glu | Leu | Ile | Gly<br>185 | Trp | Arg | Arg | Ala | Asp<br>190 | Asn | Glu |
| Leu | Asn | Tyr | Arg<br>195 | Arg | Phe | Phe | Ala | Val<br>200 | Asn | Thr | Leu | Ala | Gly<br>205 | Ile | Arg |
| Val | Glu<br>210 | Val | Pro | Pro | Val | Phe<br>215 | Asp | Glu | Ala | His | Gln<br>220 | Glu | Val | Val | Arg |
| Trp<br>225 | Phe | Arg | Ala | Gly | Leu<br>230 | Ala | Asp | Gly | Leu | Arg<br>235 | Ile | Asp | His | Pro | Asp<br>240 |
| Gly | Leu | Ala | Asp | Pro<br>245 | Glu | Gly | Tyr | Leu | Lys<br>250 | Arg | Leu | Arg | Glu | Val<br>255 | Thr |
| Gly | Gly | Ala | Tyr<br>260 | Leu | Leu | Ile | Glu | Lys<br>265 | Ile | Leu | Glu | Pro | Gly<br>270 | Glu | Gln |
| Leu | Pro | Ala | Ser<br>275 | Phe | Glu | Cys | Glu | Gly<br>280 | Thr | Thr | Gly | Tyr | Asp<br>285 | Ala | Leu |
| Ala | Asp<br>290 | Val | Asp | Arg | Val | Phe<br>295 | Val | Asp | Pro | Arg | Gly<br>300 | Gln | Val | Pro | Leu |
| Asp<br>305 | Arg | Leu | Asp | Ala | Arg<br>310 | Leu | Arg | Gly | Gly | Ala<br>315 | Pro | Ala | Asp | Tyr | Glu<br>320 |
| Asp | Met | Ile | Arg | Gly<br>325 | Thr | Lys | Arg | Arg | Ile<br>330 | Thr | Asp | Gly | Ile | Leu<br>335 | His |
| Ser | Glu | Ile | Leu<br>340 | Arg | Leu | Ala | Arg | Leu<br>345 | Val | Pro | Glu | Gln | Thr<br>350 | Gly | Ile |
| Pro | Gly | Glu<br>355 | Ala | Ala | Ala | Asp | Ala<br>360 | Ile | Ala | Glu | Ile | Ile<br>365 | Ala | Ala | Phe |
| Pro | Val | Tyr<br>370 | Arg | Ser | Tyr | Leu | Pro<br>375 | Glu | Gly | Ala | Glu | Ile<br>380 | Leu | Lys | Glu |
| Ala<br>385 | Cys | Asp | Leu | Ala | Ala<br>390 | Arg | Arg | Arg | Pro | Glu<br>395 | Leu | Gly | Gln | Thr | Val<br>400 |
| Gln | Leu | Leu | Gln | Pro<br>405 | Leu | Leu | Leu | Asp | Thr<br>410 | Asp | Leu | Glu | Ile | Ser<br>415 | Arg |
| Arg | Phe | Gln | Gln<br>420 | Thr | Ser | Gly | Met | Val<br>425 | Met | Ala | Lys | Gly | Val<br>430 | Glu | Asp |
| Thr | Ala | Phe<br>435 | Phe | Arg | Tyr | Asn | Arg<br>440 | Leu | Gly | Thr | Leu | Thr<br>445 | Glu | Val | Gly |
| Ala | Asp<br>450 | Pro | Thr | Glu | Phe | Ser<br>455 | Leu | Glu | Pro | Glu | Glu<br>460 | Phe | His | Val | Arg |
| Met<br>465 | Ala | Arg | Arg | Gln | Ala<br>470 | Glu | Leu | Pro | Leu | Ser<br>475 | Met | Thr | Thr | Leu | Ser<br>480 |
| Thr | His | Asp | Thr | Lys<br>485 | Arg | Ser | Glu | Asp | Thr<br>490 | Arg | Ala | Arg | Ile | Ser<br>495 | Val |
| Ile | Ala | Glu | Val<br>500 | Ala | Pro | Glu | Trp | Glu<br>505 | Lys | Ala | Leu | Asp | Arg<br>510 | Leu | Asn |
| Thr | Leu | Ala<br>515 | Pro | Leu | Pro | Asp | Gly<br>520 | Pro | Leu | Ser | Thr | Leu<br>525 | Leu | Trp | Gln |
| Ala | Ile<br>530 | Ala | Gly | Ala | Trp | Pro<br>535 | Ala | Ser | Arg | Glu | Arg<br>540 | Leu | Gln | Ser | Tyr |
| Ala<br>545 | Leu | Lys | Ala | Ala | Arg<br>550 | Glu | Ala | Gly | Asn | Ser<br>555 | Thr | Ser | Trp | Thr | Asp<br>560 |
| Pro | Asp | Pro | Ala | Phe<br>565 | Glu | Glu | Ala | Leu | Ser<br>570 | Ala | Val | Val | Asp | Ser<br>575 | Ala |
| Phe | Asp | Asn | Pro<br>580 | Glu | Val | Arg | Ala | Glu<br>585 | Leu | Glu | Ala | Leu | Val<br>590 | Gly | Leu |

```
Leu  Ala  Pro  His  Gly  Ala  Ser  Asn  Ser  Leu  Ala  Ala  Lys  Leu  Val  Gln
               595                 600                 605

Leu  Thr  Met  Pro  Gly  Val  Pro  Asp  Val  Tyr  Gln  Gly  Thr  Glu  Phe  Trp
          610                 615                 620

Asp  Arg  Ser  Leu  Thr  Asp  Pro  Asp  Asn  Arg  Arg  Pro  Phe  Ser  Phe  Ala
625                      630                 635                           640

Glu  Arg  Ile  Arg  Ala  Leu  Asp  Gln  Leu  Asp  Ala  Gly  His  Arg  Pro  Asp
               645                 650                           655

Ser  Phe  Gln  Asp  Glu  Ala  Val  Lys  Leu  Leu  Val  Thr  Ser  Arg  Ala  Leu
               660                 665                      670

Arg  Leu  Arg  Arg  Asn  Arg  Pro  Glu  Leu  Phe  Thr  Gly  Tyr  Arg  Pro  Val
               675                 680                      685

His  Ala  Arg  Gly  Pro  Ala  Ala  Gly  His  Leu  Val  Ala  Phe  Asp  Arg  Gly
          690                 695                 700

Ala  Gly  Gly  Val  Leu  Ala  Leu  Ala  Thr  Arg  Leu  Pro  Tyr  Gly  Leu  Glu
705                      710                 715                           720

Gln  Ser  Gly  Gly  Trp  Arg  Asp  Thr  Ala  Val  Glu  Leu  Glu  Ala  Ala  Met
               725                 730                      735

Thr  Asp  Glu  Leu  Thr  Gly  Ser  Thr  Phe  Gly  Pro  Gly  Pro  Ala  Ala  Leu
               740                 745                      750

Ser  Glu  Val  Phe  Arg  Ala  Tyr  Pro  Val  Ala  Leu  Leu  Val  Pro  Ala  Thr
          755                 760                      765

Gly  Gly  Lys  Ser
          770
```

( 2 ) INFORMATION FOR SEQ ID NO:3:

( i ) SEQUENCE CHARACTERISTICS:
        ( A ) LENGTH: 2325 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..2325

( x i ) SEQUENCE DESCRIPTION: SEQ ID NO:3:

```
ATG  AGA  ACG  CCA  GTC  TCC  ACG  TAC  AGG  CTG  CAG  ATC  AGG  AAG  GGA  TTC    48
Met  Arg  Thr  Pro  Val  Ser  Thr  Tyr  Arg  Leu  Gln  Ile  Arg  Lys  Gly  Phe
          775                 780                 785

ACA  CTC  TTC  GAC  GCG  GCC  AAA  ACC  GTT  CCG  TAC  CTG  CAC  TCG  CTC  GGC    96
Thr  Leu  Phe  Asp  Ala  Ala  Lys  Thr  Val  Pro  Tyr  Leu  His  Ser  Leu  Gly
          790                 795                 800

GTC  GAC  TGG  GTC  TAC  CTT  TCT  CCG  GTC  CTG  ACT  GCC  GAG  CAG  GGC  TCC   144
Val  Asp  Trp  Val  Tyr  Leu  Ser  Pro  Val  Leu  Thr  Ala  Glu  Gln  Gly  Ser
805                      810                 815                           820

GAC  CAC  GGG  TAC  GAC  GTC  ACC  GAT  CCC  TCC  GCC  GTC  GAC  CCC  GAA  CGC   192
Asp  His  Gly  Tyr  Asp  Val  Thr  Asp  Pro  Ser  Ala  Val  Asp  Pro  Glu  Arg
               825                 830                 835

GGC  GGG  CCG  GAG  GGC  CTC  GCG  GCG  GTT  TCC  AAG  GCG  GCC  CGC  GCC  GCG   240
Gly  Gly  Pro  Glu  Gly  Leu  Ala  Ala  Val  Ser  Lys  Ala  Ala  Arg  Ala  Ala
               840                 845                 850

GGC  ATG  GGC  GTG  CTG  ATC  GAC  ATC  GTG  CCC  AAC  CAC  GTG  GGC  GTC  GCG   288
Gly  Met  Gly  Val  Leu  Ile  Asp  Ile  Val  Pro  Asn  His  Val  Gly  Val  Ala
          855                 860                 865

ACG  CCG  GCG  CAG  AAC  CCC  TGG  TGG  TGG  TCG  CTG  CTC  AAG  GAG  GGA  CGC   336
Thr  Pro  Ala  Gln  Asn  Pro  Trp  Trp  Trp  Ser  Leu  Leu  Lys  Glu  Gly  Arg
          870                 875                 880
```

| | | | | | | | | | | | | | | | | |
|---|---|---|---|---|---|---|---|---|---|---|---|---|---|---|---|---|
| CAG | TCC | CGT | TAC | GCG | GAG | GCG | TTC | GAC | GTC | GAT | TGG | GAC | CTC | GCC | GGG | 384 |
| Gln | Ser | Arg | Tyr | Ala | Glu | Ala | Phe | Asp | Val | Asp | Trp | Asp | Leu | Ala | Gly | |
| 885 | | | | 890 | | | | | 895 | | | | | 900 | | |
| GGA | CGC | ATC | CGG | CTG | CCG | GTG | CTC | GGC | AGC | GAC | GAT | GAC | CTC | GAC | CAG | 432 |
| Gly | Arg | Ile | Arg | Leu | Pro | Val | Leu | Gly | Ser | Asp | Asp | Asp | Leu | Asp | Gln | |
| | | | | 905 | | | | | 910 | | | | | 915 | | |
| CTC | GAA | ATC | AGG | GAC | GGG | GAG | CTG | CGG | TAC | TAC | GAC | CAC | CGA | TTC | CCG | 480 |
| Leu | Glu | Ile | Arg | Asp | Gly | Glu | Leu | Arg | Tyr | Tyr | Asp | His | Arg | Phe | Pro | |
| | | | 920 | | | | | 925 | | | | | 930 | | | |
| CTC | GCC | GAG | GGA | ACC | TAC | GCC | GAA | GGC | GAC | GCC | CCG | CGG | GAT | GTC | CAC | 528 |
| Leu | Ala | Glu | Gly | Thr | Tyr | Ala | Glu | Gly | Asp | Ala | Pro | Arg | Asp | Val | His | |
| | | | 935 | | | | | 940 | | | | | 945 | | | |
| GCC | CGG | CAG | CAC | TAC | GAG | CTC | ATC | GGC | TGG | CGC | CGC | GCG | GAC | AAC | GAG | 576 |
| Ala | Arg | Gln | His | Tyr | Glu | Leu | Ile | Gly | Trp | Arg | Arg | Ala | Asp | Asn | Glu | |
| | | | 950 | | | | | 955 | | | | | 960 | | | |
| CTG | AAC | TAC | CGC | CGC | TTT | TTC | GCG | GTG | AAC | ACG | CTC | GCC | GGC | GTC | CGC | 624 |
| Leu | Asn | Tyr | Arg | Arg | Phe | Phe | Ala | Val | Asn | Thr | Leu | Ala | Gly | Val | Arg | |
| 965 | | | | | 970 | | | | | 975 | | | | | 980 | |
| GTG | GAA | ATC | CCC | GCC | GTC | TTC | GAC | GAG | GCA | CAC | CAG | GAG | GTG | GTG | CGC | 672 |
| Val | Glu | Ile | Pro | Ala | Val | Phe | Asp | Glu | Ala | His | Gln | Glu | Val | Val | Arg | |
| | | | | 985 | | | | | 990 | | | | | 995 | | |
| TGG | TTC | CGC | GAG | GAC | CTT | GCG | GAC | GGC | CTG | CGG | ATC | GAC | CAC | CCG | GAC | 720 |
| Trp | Phe | Arg | Glu | Asp | Leu | Ala | Asp | Gly | Leu | Arg | Ile | Asp | His | Pro | Asp | |
| | | | | 1000 | | | | | 1005 | | | | | 1010 | | |
| GGC | CTC | GCT | GAC | CCC | GAG | GGG | TAC | CTG | AAG | CGA | CTC | CGG | GAA | GTC | ACC | 768 |
| Gly | Leu | Ala | Asp | Pro | Glu | Gly | Tyr | Leu | Lys | Arg | Leu | Arg | Glu | Val | Thr | |
| | | | | 1015 | | | | | 1020 | | | | | 1025 | | |
| GGC | GGC | GCT | TAC | CTG | CTG | ATC | GAA | AAG | ATC | CTG | GAG | CCG | GGG | GAG | CAG | 816 |
| Gly | Gly | Ala | Tyr | Leu | Leu | Ile | Glu | Lys | Ile | Leu | Glu | Pro | Gly | Glu | Gln | |
| | | | | 1030 | | | | | 1035 | | | | | 1040 | | |
| CTG | CCC | GCC | AGC | TTC | GAG | TGT | GAA | GGC | ACC | ACA | GGC | TAC | GAC | GCC | CTC | 864 |
| Leu | Pro | Ala | Ser | Phe | Glu | Cys | Glu | Gly | Thr | Thr | Gly | Tyr | Asp | Ala | Leu | |
| 1045 | | | | | 1050 | | | | | 1055 | | | | | 1060 | |
| GCC | GAC | GTC | GAC | CGG | GTT | CTC | GTG | GAC | CCG | CGC | GGC | CAG | GAA | CCG | CTG | 912 |
| Ala | Asp | Val | Asp | Arg | Val | Leu | Val | Asp | Pro | Arg | Gly | Gln | Glu | Pro | Leu | |
| | | | | 1065 | | | | | 1070 | | | | | 1075 | | |
| GAC | CGG | CTT | GAC | GCG | TCC | CTG | CGT | GGC | GGC | GAG | CCC | GCC | GAC | TAC | CAG | 960 |
| Asp | Arg | Leu | Asp | Ala | Ser | Leu | Arg | Gly | Gly | Glu | Pro | Ala | Asp | Tyr | Gln | |
| | | | | 1080 | | | | | 1085 | | | | | 1090 | | |
| GAC | ATG | ATC | CGC | GGA | ACC | AAG | CGC | CGG | ATC | ACC | GAC | GGT | ATC | CTG | CAC | 1008 |
| Asp | Met | Ile | Arg | Gly | Thr | Lys | Arg | Arg | Ile | Thr | Asp | Gly | Ile | Leu | His | |
| | | | | 1095 | | | | | 1100 | | | | | 1105 | | |
| TCG | GAG | ATC | CTG | CGG | CTG | GCC | CGG | CTG | GTT | CCG | GGC | GAC | GCC | AAC | GTT | 1056 |
| Ser | Glu | Ile | Leu | Arg | Leu | Ala | Arg | Leu | Val | Pro | Gly | Asp | Ala | Asn | Val | |
| | | | | 1110 | | | | | 1115 | | | | | 1120 | | |
| TCA | ATC | GAC | GCC | GGA | GCC | GAC | GCT | CTC | GCC | GAA | ATC | ATC | GCC | GCC | TTC | 1104 |
| Ser | Ile | Asp | Ala | Gly | Ala | Asp | Ala | Leu | Ala | Glu | Ile | Ile | Ala | Ala | Phe | |
| 1125 | | | | | 1130 | | | | | 1135 | | | | | 1140 | |
| CCG | GTC | TAC | CGC | ACC | TAC | CTG | CCG | GAG | GGC | GCC | GAG | GTC | CTG | AAG | GAG | 1152 |
| Pro | Val | Tyr | Arg | Thr | Tyr | Leu | Pro | Glu | Gly | Ala | Glu | Val | Leu | Lys | Glu | |
| | | | | 1145 | | | | | 1150 | | | | | 1155 | | |
| GCG | TGC | GAG | CTT | GCC | GCG | CGT | AGG | CGG | CCG | GAA | CTC | GAC | CAG | GCC | ATC | 1200 |
| Ala | Cys | Glu | Leu | Ala | Ala | Arg | Arg | Arg | Pro | Glu | Leu | Asp | Gln | Ala | Ile | |
| | | | | 1160 | | | | | 1165 | | | | | 1170 | | |
| CAG | GCT | CTG | CAG | CCG | CTG | CTG | CTG | GAC | ACG | GAC | CTC | GAG | CTT | GCC | CGG | 1248 |
| Gln | Ala | Leu | Gln | Pro | Leu | Leu | Leu | Asp | Thr | Asp | Leu | Glu | Leu | Ala | Arg | |
| | | | | 1175 | | | | | 1180 | | | | | 1185 | | |
| CGC | TTC | CAG | CAG | ACC | TCG | GGC | ATG | GTC | ATG | GCC | AAG | GGC | GTG | GAG | GAC | 1296 |
| Arg | Phe | Gln | Gln | Thr | Ser | Gly | Met | Val | Met | Ala | Lys | Gly | Val | Glu | Asp | |
| | | | | 1190 | | | | | 1195 | | | | | 1200 | | |

-continued

```
ACC GCG TTC TTC CGC TAC AAC CGC CTG GGC ACC CTC ACG GAA GTG GGC      1344
Thr Ala Phe Phe Arg Tyr Asn Arg Leu Gly Thr Leu Thr Glu Val Gly
1205                    1210                1215                1220

GCC GAC CCC ACC GAG TTC GCC GTG GAG CCG GAC GAG TTC CAC GCC CGG      1392
Ala Asp Pro Thr Glu Phe Ala Val Glu Pro Asp Glu Phe His Ala Arg
                    1225                1230                1235

CTG GCA CGC CGG CAG GCC GAG CTT CCG CTG TCC ATG ACG ACG CTG AGC      1440
Leu Ala Arg Arg Gln Ala Glu Leu Pro Leu Ser Met Thr Thr Leu Ser
                1240                1245                1250

ACG CAC GAC ACC AAG CGC AGC GAG GAC ACC CGA GCA AGG ATT TCG GTC      1488
Thr His Asp Thr Lys Arg Ser Glu Asp Thr Arg Ala Arg Ile Ser Val
            1255                1260                1265

ATT TCC GAG GTT GCG GGT GAC TGG GAA AAG GCC TTG AAC CGG CTG CGC      1536
Ile Ser Glu Val Ala Gly Asp Trp Glu Lys Ala Leu Asn Arg Leu Arg
        1270                1275                1280

GAC CTG GCC CCG CTG CCG GAC GGC CCG CTG TCC GCG CTG CTC TGG CAG      1584
Asp Leu Ala Pro Leu Pro Asp Gly Pro Leu Ser Ala Leu Leu Trp Gln
1285                1290                1295                1300

GCC ATT GCC GGC GCC TGG CCC GCC AGC CGG GAA CGC CTG CAG TAC TAC      1632
Ala Ile Ala Gly Ala Trp Pro Ala Ser Arg Glu Arg Leu Gln Tyr Tyr
                    1305                1310                1315

GCG CTG AAG GCC GCG CGT GAA GCG GGG AAC TCG ACC AAC TGG ACC GAT      1680
Ala Leu Lys Ala Ala Arg Glu Ala Gly Asn Ser Thr Asn Trp Thr Asp
                1320                1325                1330

CCG GCC CCC GCG TTC GAG GAG AAG CTG AAG GCC GCG GTC GAC GCC GTG      1728
Pro Ala Pro Ala Phe Glu Glu Lys Leu Lys Ala Ala Val Asp Ala Val
            1335                1340                1345

TTC GAC AAT CCC GCC GTG CAG GCC GAG GTG GAA GCC CTC GTC GAG CTC      1776
Phe Asp Asn Pro Ala Val Gln Ala Glu Val Glu Ala Leu Val Glu Leu
        1350                1355                1360

CTG GAG CCG TAC GGA GCT TCG AAC TCC CTC GCC GCC AAG CTC GTG CAG      1824
Leu Glu Pro Tyr Gly Ala Ser Asn Ser Leu Ala Ala Lys Leu Val Gln
1365                1370                1375                1380

CTG ACC ATG CCC GGC GTC CCG GAC GTC TAC CAG GGC ACG GAG TTC TGG      1872
Leu Thr Met Pro Gly Val Pro Asp Val Tyr Gln Gly Thr Glu Phe Trp
                    1385                1390                1395

GAC CGG TCG CTG ACG GAC CCG GAC AAC CGG CGG CCG TTC AGC TTC GAC      1920
Asp Arg Ser Leu Thr Asp Pro Asp Asn Arg Arg Pro Phe Ser Phe Asp
                1400                1405                1410

GAC CGC CGC GCC GCG CTG GAG CAG CTG GAT GCC GGC GAC CTT CCC GCG      1968
Asp Arg Arg Ala Ala Leu Glu Gln Leu Asp Ala Gly Asp Leu Pro Ala
            1415                1420                1425

TCA TTT ACC GAT GAG CGG ACG AAG CTG CTA GTG ACG TCG CGC GCG CTG      2016
Ser Phe Thr Asp Glu Arg Thr Lys Leu Leu Val Thr Ser Arg Ala Leu
        1430                1435                1440

CGG CTG CGC CGG GAC CGT CCG GAG CTG TTC ACG GGG TAC CGG CCG GTC      2064
Arg Leu Arg Arg Asp Arg Pro Glu Leu Phe Thr Gly Tyr Arg Pro Val
1445                1450                1455                1460

CTG GCC AGC GGG CCC GCC GCC GGG CAC CTG CTC GCG TTC GAC CGC GGC      2112
Leu Ala Ser Gly Pro Ala Ala Gly His Leu Leu Ala Phe Asp Arg Gly
                    1465                1470                1475

ACC GCG GCG GCG CCG GGT GCA TTG ACC CTC GCC ACG CGG CTT CCC TAC      2160
Thr Ala Ala Ala Pro Gly Ala Leu Thr Leu Ala Thr Arg Leu Pro Tyr
                1480                1485                1490

GGG CTG GAA CAG TCG GGT GGA TGG CGG GAC ACC GCC GTC GAA CTT AAC      2208
Gly Leu Glu Gln Ser Gly Gly Trp Arg Asp Thr Ala Val Glu Leu Asn
            1495                1500                1505

ACC GCC ATG AAA GAC GAA CTG ACC GGT GCC GGC TTC GGA CCG GGG GCA      2256
Thr Ala Met Lys Asp Glu Leu Thr Gly Ala Gly Phe Gly Pro Gly Ala
        1510                1515                1520
```

```
GTG AAG ATC GCC GAC ATC TTC CGG TCG TTC CCC GTT GCG CTG CTG GTG     2304
Val Lys Ile Ala Asp Ile Phe Arg Ser Phe Pro Val Ala Leu Leu Val
1525            1530                1535                1540

CCG CAG ACA GGA GGA GAG TCA                                          2325
Pro Gln Thr Gly Gly Glu Ser
                1545
```

( 2 ) INFORMATION FOR SEQ ID NO:4:

( i ) SEQUENCE CHARACTERISTICS:
        ( A ) LENGTH: 775 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Arg Thr Pro Val Ser Thr Tyr Arg Leu Gln Ile Arg Lys Gly Phe
 1               5                  10                  15

Thr Leu Phe Asp Ala Ala Lys Thr Val Pro Tyr Leu His Ser Leu Gly
                20                  25                  30

Val Asp Trp Val Tyr Leu Ser Pro Val Leu Thr Ala Glu Gln Gly Ser
            35                  40                  45

Asp His Gly Tyr Asp Val Thr Asp Pro Ser Ala Val Asp Pro Glu Arg
        50                  55                  60

Gly Gly Pro Glu Gly Leu Ala Ala Val Ser Lys Ala Ala Arg Ala Ala
 65                 70                  75                  80

Gly Met Gly Val Leu Ile Asp Ile Val Pro Asn His Val Gly Val Ala
                85                  90                  95

Thr Pro Ala Gln Asn Pro Trp Trp Trp Ser Leu Leu Lys Glu Gly Arg
            100                 105                 110

Gln Ser Arg Tyr Ala Glu Ala Phe Asp Val Asp Trp Asp Leu Ala Gly
        115                 120                 125

Gly Arg Ile Arg Leu Pro Val Leu Gly Ser Asp Asp Leu Asp Gln
        130                 135                 140

Leu Glu Ile Arg Asp Gly Glu Leu Arg Tyr Tyr Asp His Arg Phe Pro
145                 150                 155                 160

Leu Ala Glu Gly Thr Tyr Ala Glu Gly Asp Ala Pro Arg Asp Val His
                165                 170                 175

Ala Arg Gln His Tyr Glu Leu Ile Gly Trp Arg Arg Ala Asp Asn Glu
            180                 185                 190

Leu Asn Tyr Arg Arg Phe Phe Ala Val Asn Thr Leu Ala Gly Val Arg
        195                 200                 205

Val Glu Ile Pro Ala Val Phe Asp Glu Ala His Gln Glu Val Val Arg
    210                 215                 220

Trp Phe Arg Glu Asp Leu Ala Asp Gly Leu Arg Ile Asp His Pro Asp
225                 230                 235                 240

Gly Leu Ala Asp Pro Glu Gly Tyr Leu Lys Arg Leu Arg Glu Val Thr
                245                 250                 255

Gly Gly Ala Tyr Leu Leu Ile Glu Lys Ile Leu Glu Pro Gly Glu Gln
            260                 265                 270

Leu Pro Ala Ser Phe Glu Cys Glu Gly Thr Thr Gly Tyr Asp Ala Leu
        275                 280                 285

Ala Asp Val Asp Arg Val Leu Val Asp Pro Arg Gly Gln Glu Pro Leu
    290                 295                 300

Asp Arg Leu Asp Ala Ser Leu Arg Gly Gly Glu Pro Ala Asp Tyr Gln
305                 310                 315                 320
```

```
Asp Met Ile Arg Gly Thr Lys Arg Arg Ile Thr Asp Gly Ile Leu His
                325                 330                 335

Ser Glu Ile Leu Arg Leu Ala Arg Leu Val Pro Gly Asp Ala Asn Val
            340                 345                 350

Ser Ile Asp Ala Gly Ala Asp Ala Leu Ala Glu Ile Ile Ala Ala Phe
        355                 360                 365

Pro Val Tyr Arg Thr Tyr Leu Pro Glu Gly Ala Glu Val Leu Lys Glu
    370                 375                 380

Ala Cys Glu Leu Ala Ala Arg Arg Arg Pro Glu Leu Asp Gln Ala Ile
385                 390                 395                 400

Gln Ala Leu Gln Pro Leu Leu Leu Asp Thr Asp Leu Glu Leu Ala Arg
            405                 410                 415

Arg Phe Gln Gln Thr Ser Gly Met Val Met Ala Lys Gly Val Glu Asp
        420                 425                 430

Thr Ala Phe Phe Arg Tyr Asn Arg Leu Gly Thr Leu Thr Glu Val Gly
    435                 440                 445

Ala Asp Pro Thr Glu Phe Ala Val Glu Pro Asp Glu Phe His Ala Arg
    450                 455                 460

Leu Ala Arg Arg Gln Ala Glu Leu Pro Leu Ser Met Thr Thr Leu Ser
465                 470                 475                 480

Thr His Asp Thr Lys Arg Ser Glu Asp Thr Arg Ala Arg Ile Ser Val
            485                 490                 495

Ile Ser Glu Val Ala Gly Asp Trp Glu Lys Ala Leu Asn Arg Leu Arg
            500                 505                 510

Asp Leu Ala Pro Leu Pro Asp Gly Pro Leu Ser Ala Leu Leu Trp Gln
            515                 520                 525

Ala Ile Ala Gly Ala Trp Pro Ala Ser Arg Glu Arg Leu Gln Tyr Tyr
    530                 535                 540

Ala Leu Lys Ala Ala Arg Glu Ala Gly Asn Ser Thr Asn Trp Thr Asp
545                 550                 555                 560

Pro Ala Pro Ala Phe Glu Glu Lys Leu Lys Ala Ala Val Asp Ala Val
                565                 570                 575

Phe Asp Asn Pro Ala Val Gln Ala Glu Val Glu Ala Leu Val Glu Leu
            580                 585                 590

Leu Glu Pro Tyr Gly Ala Ser Asn Ser Leu Ala Ala Lys Leu Val Gln
        595                 600                 605

Leu Thr Met Pro Gly Val Pro Asp Val Tyr Gln Gly Thr Glu Phe Trp
    610                 615                 620

Asp Arg Ser Leu Thr Asp Pro Asp Asn Arg Arg Pro Phe Ser Phe Asp
625                 630                 635                 640

Asp Arg Arg Ala Ala Leu Glu Gln Leu Asp Ala Gly Asp Leu Pro Ala
                645                 650                 655

Ser Phe Thr Asp Glu Arg Thr Lys Leu Leu Val Thr Ser Arg Ala Leu
            660                 665                 670

Arg Leu Arg Arg Asp Arg Pro Glu Leu Phe Thr Gly Tyr Arg Pro Val
            675                 680                 685

Leu Ala Ser Gly Pro Ala Ala Gly His Leu Leu Ala Phe Asp Arg Gly
    690                 695                 700

Thr Ala Ala Ala Pro Gly Ala Leu Thr Leu Ala Thr Arg Leu Pro Tyr
705                 710                 715                 720

Gly Leu Glu Gln Ser Gly Gly Trp Arg Asp Thr Ala Val Glu Leu Asn
            725                 730                 735

Thr Ala Met Lys Asp Glu Leu Thr Gly Ala Gly Phe Gly Pro Gly Ala
```

|   |   |   | 740 |   |   |   |   |   | 745 |   |   |   |   | 750 |   |   |
|---|---|---|---|---|---|---|---|---|---|---|---|---|---|---|---|---|
| Val | Lys | Ile | Ala | Asp | Ile | Phe | Arg | Ser | Phe | Pro | Val | Ala | Leu | Leu | Val |
|   |   |   | 755 |   |   |   |   |   | 760 |   |   |   |   | 765 |   |   |
| Pro | Gln | Thr | Gly | Gly | Glu | Ser |   |   |   |   |   |   |   |   |   |
|   |   |   | 770 |   |   |   |   |   | 775 |   |   |   |   |   |   |

( 2 ) INFORMATION FOR SEQ ID NO:5:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:5:

CCNGARTGGG ARAA      14

( 2 ) INFORMATION FOR SEQ ID NO:6:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:6:

ACNGARTTYT GGGA      14

( 2 ) INFORMATION FOR SEQ ID NO:7:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:7:

GTAAAACGAC GGCCAGT      17

( 2 ) INFORMATION FOR SEQ ID NO:8:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:8:

TTYGAYGTNG AYTGGGA      17

( 2 ) INFORMATION FOR SEQ ID NO:9:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:9:

ACNGARTTYT GGGA                                                                                              14

(2) INFORMATION FOR SEQ ID NO:10:

(i) SEQUENCE CHARACTERISTICS:
        (A) LENGTH: 2936 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 565..2880

(xi) SEQUENCE DESCRIPTION: SEQ ID NO:10:

```
CGTGCTCTAC TTCAACGCGC ACGACGGCGA CGTCGTGTTC AAGCTCCCGT CGGATGAATA      60

CGCCCCGGCC TGGGACGTCA TCATCGACAC CGCCGGCGCG GGTGCCGATT CCGAACCCGT     120

GCAGGCTGGC GGCAAACTCA CCGTGGCAGC GAAATCGCTC GTGGTGCTCC GTGCCCACAG     180

CGCCCCGGAG GAGGAACCGG ACCACTCGGT GGCCGCCTCC CTCGCAGCGC TGACGCAGAC     240

TGCGACCGCC GAAACCGCGG CGCTCACCGC CCCCACCGTT CCGGAGCCGA GGAAGACCAA     300

GAAGGCAGCG CCGAAGCCGG AAGAGGAGGC TCCCGACGAG GCGGCGCCGA AGCCGGAAGA     360

GAAGGCTCCC GACGAGGCGG CGGCGAAGCC GGAAGAGGCT GCTTCCGACG AGGCGGCGGC     420

GAAGCCGGAA GAGAAGGCTC CCGACGAGGC GGCGGCGAAG CCGGAAGAGG CTGCTTCCGA     480

CGAGGCGGCG GCGAAGCCCG CGGGGAAGGC AGCGGCCAAA ACGGCCGGCA GGCGAGCGCC     540

AGGCAAGCAG GGCGGGACGG GCTC ATG AGG ACA CCC GCC TCG ACC TAC CGG       591
                             Met Arg Thr Pro Ala Ser Thr Tyr Arg
                                                            780
```

```
CTG CAG ATC AGG CGG GGT TTC ACG CTG TTT GAT GCC GCC GAG ACC GTG      639
Leu Gln Ile Arg Arg Gly Phe Thr Leu Phe Asp Ala Ala Glu Thr Val
785                 790                 795                 800
```

```
CCC TAC CTG AAG TCA CTC GGG GTG GAC TGG ATC TAC CTG TCG CCC ATC      687
Pro Tyr Leu Lys Ser Leu Gly Val Asp Trp Ile Tyr Leu Ser Pro Ile
            805                 810                 815
```

```
CTG AAG GCA GAG AGC GGC TCC GAC CAC GGC TAT GAC GTC ACC GAT CCC      735
Leu Lys Ala Glu Ser Gly Ser Asp His Gly Tyr Asp Val Thr Asp Pro
            820                 825                 830
```

```
GCC GTA GTG GAC CCG GAG CGC GGC GGC CCT GAA GGG CTG GCC GCG GTG      783
Ala Val Val Asp Pro Glu Arg Gly Gly Pro Glu Gly Leu Ala Ala Val
                835                 840                 845
```

```
TCC AAG GCG GCC CGC GGT GCC GGC ATG GGC GTG CTG ATC GAC ATC GTG      831
Ser Lys Ala Ala Arg Gly Ala Gly Met Gly Val Leu Ile Asp Ile Val
    850                 855                 860
```

```
CCG AAC CAC GTG GGC GTG GCG TCG CCG CCG CAG AAC CCG TGG TGG TGG      879
Pro Asn His Val Gly Val Ala Ser Pro Pro Gln Asn Pro Trp Trp Trp
865                 870                 875                 880
```

```
TCG CTG CTC AAG GAA GGG CGC GGG TCG CCC TAC GCC GTG GCG TTC GAC      927
Ser Leu Leu Lys Glu Gly Arg Gly Ser Pro Tyr Ala Val Ala Phe Asp
                885                 890                 895
```

```
GTC GAC TGG GAC CTG GCG GGG GGC CGC ATC CGG ATC CCC GTC CTG GGC      975
Val Asp Trp Asp Leu Ala Gly Gly Arg Ile Arg Ile Pro Val Leu Gly
                900                 905                 910
```

```
AGC GAC GAC GAT CTG GAC CAG CTC GAA ATC AAG GAC GGC GAG CTG CGG     1023
Ser Asp Asp Asp Leu Asp Gln Leu Glu Ile Lys Asp Gly Glu Leu Arg
                915                 920                 925
```

```
TAC TAC GAC CAC CGC TTC CCG CTG GCC GAG GGC AGC TAC CGG GAC GGC     1071
Tyr Tyr Asp His Arg Phe Pro Leu Ala Glu Gly Ser Tyr Arg Asp Gly
```

-continued

```
                       930                            935                              940
GAC  TCC  CCG  CAG  GAC  GTC  CAC  GGC  CGG  CAG  CAC  TAC  GAA  CTC  ATC  GGC    1119
Asp  Ser  Pro  Gln  Asp  Val  His  Gly  Arg  Gln  His  Tyr  Glu  Leu  Ile  Gly
945                 950                            955                          960

TGG  CGG  CGC  GCC  GAC  AAT  GAA  CTG  AAC  TAC  CGC  GGG  TTC  TTC  GCG  GTG    1167
Trp  Arg  Arg  Ala  Asp  Asn  Glu  Leu  Asn  Tyr  Arg  Arg  Phe  Phe  Ala  Val
                    965                            970                          975

AAC  ACG  CTC  GCC  GGC  ATC  CGG  GTG  GAG  GTG  CCG  CCG  GTC  TTC  GAT  GAA    1215
Asn  Thr  Leu  Ala  Gly  Ile  Arg  Val  Glu  Val  Pro  Pro  Val  Phe  Asp  Glu
                    980                            985                          990

GCG  CAC  CAG  GAG  GTG  GTG  CGC  TGG  TTC  CGT  GCG  GGG  CTC  GCC  GAC  GGG    1263
Ala  His  Gln  Glu  Val  Val  Arg  Trp  Phe  Arg  Ala  Gly  Leu  Ala  Asp  Gly
                    995                            1000                         1005

CTG  CGG  ATC  GAC  CAC  CCG  GAC  GGC  CTG  GCC  GAT  CCC  GAG  GGG  TAT  TTG    1311
Leu  Arg  Ile  Asp  His  Pro  Asp  Gly  Leu  Ala  Asp  Pro  Glu  Gly  Tyr  Leu
1010                     1015                          1020

AAG  CGG  CTC  CGT  GAG  GTC  ACC  GGG  GGC  GCG  TAC  CTG  CTC  ATC  GAA  AAG    1359
Lys  Arg  Leu  Arg  Glu  Val  Thr  Gly  Gly  Ala  Tyr  Leu  Leu  Ile  Glu  Lys
1025                     1030                          1035                      1040

ATC  CTC  GAG  CCG  GGC  GAA  CAG  TTG  CCG  GCC  AGC  TTC  GAG  TGC  GAA  GGC    1407
Ile  Leu  Glu  Pro  Gly  Glu  Gln  Leu  Pro  Ala  Ser  Phe  Glu  Cys  Glu  Gly
                         1045                          1050                      1055

ACC  ACC  GGC  TAC  GAC  GCC  CTC  GCG  GAT  GTC  GAC  AGG  GTC  TTC  GTG  GAC    1455
Thr  Thr  Gly  Tyr  Asp  Ala  Leu  Ala  Asp  Val  Asp  Arg  Val  Phe  Val  Asp
                    1060                           1065                          1070

CCG  CGG  GGA  CAG  GTG  CCG  CTG  GAC  CGT  CTG  GAC  GCA  GGG  CTG  CGC  GGC    1503
Pro  Arg  Gly  Gln  Val  Pro  Leu  Asp  Arg  Leu  Asp  Ala  Arg  Leu  Arg  Gly
                    1075                           1080                          1085

GGT  GCG  CCG  GCC  GAC  TAC  GAG  GAC  ATG  ATC  CGC  GGG  ACC  AAG  CGC  CGG    1551
Gly  Ala  Pro  Ala  Asp  Tyr  Glu  Asp  Met  Ile  Arg  Gly  Thr  Lys  Arg  Arg
1090                     1095                          1100

ATC  ACC  GAC  GGC  ATC  CTG  CAC  TCC  GAG  ATC  CTG  CGC  CTT  GCC  AGG  CTG    1599
Ile  Thr  Asp  Gly  Ile  Leu  His  Ser  Glu  Ile  Leu  Arg  Leu  Ala  Arg  Leu
1105                     1110                          1115                      1120

GTG  CCC  GAG  CAG  ACC  GGA  ATT  CCC  GGG  GAG  GCG  GCC  GCG  GAT  GCG  ATC    1647
Val  Pro  Glu  Gln  Thr  Gly  Ile  Pro  Gly  Glu  Ala  Ala  Ala  Asp  Ala  Ile
                    1125                           1130                          1135

GCG  GAG  ATC  ATC  GCG  GCC  TTC  CCG  GTC  TAC  CGG  TCC  TAT  CTT  CCC  GAG    1695
Ala  Glu  Ile  Ile  Ala  Ala  Phe  Pro  Val  Tyr  Arg  Ser  Tyr  Leu  Pro  Glu
                    1140                           1145                          1150

GGC  GCG  GAG  ATC  CTG  AAG  GAG  GCC  TGC  GAC  CTC  GCC  GCG  CGG  AGG  CGT    1743
Gly  Ala  Glu  Ile  Leu  Lys  Glu  Ala  Cys  Asp  Leu  Ala  Ala  Arg  Arg  Arg
                    1155                           1160                          1165

CCG  GAA  CTG  GGC  CAG  ACC  GTC  CAG  CTG  CTG  CAG  CCG  CTG  CTG  CTG  GAT    1791
Pro  Glu  Leu  Gly  Gln  Thr  Val  Gln  Leu  Leu  Gln  Pro  Leu  Leu  Leu  Asp
                    1170                           1175                          1180

ACC  GAC  CTC  GAG  ATT  TCC  CGC  AGG  TTC  CAG  CAG  ACC  TCG  GGA  ATG  GTC    1839
Thr  Asp  Leu  Glu  Ile  Ser  Arg  Arg  Phe  Gln  Gln  Thr  Ser  Gly  Met  Val
1185                     1190                          1195                      1200

ATG  GCC  AAA  GGC  GTG  GAG  GAC  ACC  GCG  TTC  TTC  CGC  TAC  AAC  CGG  CTG    1887
Met  Ala  Lys  Gly  Val  Glu  Asp  Thr  Ala  Phe  Phe  Arg  Tyr  Asn  Arg  Leu
                    1205                           1210                          1215

GGA  ACG  CTC  ACC  GAG  GTG  GGC  GCC  GAC  CCC  ACC  GAG  TTC  TCG  CTG  GAA    1935
Gly  Thr  Leu  Thr  Glu  Val  Gly  Ala  Asp  Pro  Thr  Glu  Phe  Ser  Leu  Glu
                    1220                           1225                          1230

CCG  GAG  GAG  TTT  CAC  GTC  CGG  ATG  GCC  CGC  CGG  CAG  GCC  GAA  CTC  CCG    1983
Pro  Glu  Glu  Phe  His  Val  Arg  Met  Ala  Arg  Arg  Gln  Ala  Glu  Leu  Pro
                    1235                           1240                          1245

CTC  TCC  ATG  ACC  ACC  CTG  AGC  ACG  CAC  GAC  ACC  AAG  CGC  AGC  GAG  GAC    2031
Leu  Ser  Met  Thr  Thr  Leu  Ser  Thr  His  Asp  Thr  Lys  Arg  Ser  Glu  Asp
```

|  |  |  |  |  |  |  |  |  |  |  |  |  |  |  |  |
|---|---|---|---|---|---|---|---|---|---|---|---|---|---|---|---|
| | | | 1250 | | | | | 1255 | | | | | 1260 | | |

```
ACC  CGG  GCC  CGG  ATC  TCG  GTG  ATC  GCC  GAG  GTC  GCG  CCT  GAA  TGG  GAA         2079
Thr  Arg  Ala  Arg  Ile  Ser  Val  Ile  Ala  Glu  Val  Ala  Pro  Glu  Trp  Glu
1265                1270                1275                     1280

AAG  GCC  CTG  GAC  AGG  CTG  AAC  ACC  CTC  GCT  CCG  CTG  CCG  GAC  GGC  CCG         2127
Lys  Ala  Leu  Asp  Arg  Leu  Asn  Thr  Leu  Ala  Pro  Leu  Pro  Asp  Gly  Pro
                    1285                1290                     1295

CTC  TCC  ACG  CTG  CTC  TGG  CAG  GCG  ATT  GCG  GGG  GCA  TGG  CCG  GCC  AGC         2175
Leu  Ser  Thr  Leu  Leu  Trp  Gln  Ala  Ile  Ala  Gly  Ala  Trp  Pro  Ala  Ser
               1300                1305                     1310

CGG  GAA  CGC  CTT  CAG  TCC  TAC  GCC  CTG  AAA  GCG  GCG  CGC  GAA  GCC  GGG         2223
Arg  Glu  Arg  Leu  Gln  Ser  Tyr  Ala  Leu  Lys  Ala  Ala  Arg  Glu  Ala  Gly
               1315                1320                     1325

AAC  TCG  ACC  AGC  TGG  ACC  GAT  CCG  GAC  CCG  GCA  TTC  GAG  GAG  GCA  CTT         2271
Asn  Ser  Thr  Ser  Trp  Thr  Asp  Pro  Asp  Pro  Ala  Phe  Glu  Glu  Ala  Leu
1330                1335                1340

TCC  GCC  GTC  GTC  GAC  TCC  GCC  TTC  GAC  AAT  CCG  GAG  GTG  CGT  GCG  GAA         2319
Ser  Ala  Val  Val  Asp  Ser  Ala  Phe  Asp  Asn  Pro  Glu  Val  Arg  Ala  Glu
1345                1350                1355                     1360

CTT  GAG  GCC  CTG  GTG  GGC  CTC  CTT  GCG  CCG  CAC  GGT  GCG  TCC  AAC  TCG         2367
Leu  Glu  Ala  Leu  Val  Gly  Leu  Leu  Ala  Pro  His  Gly  Ala  Ser  Asn  Ser
                    1365                1370                     1375

CTC  GCG  GCA  AAG  CTT  GTC  CAG  CTG  ACC  ATG  CCG  GGC  GTT  CCG  GAC  GTG         2415
Leu  Ala  Ala  Lys  Leu  Val  Gln  Leu  Thr  Met  Pro  Gly  Val  Pro  Asp  Val
               1380                1385                     1390

TAC  CAG  GGC  ACC  GAG  TTC  TGG  GAC  AGG  TCG  CTG  ACC  GAT  CCG  GAC  AAC         2463
Tyr  Gln  Gly  Thr  Glu  Phe  Trp  Asp  Arg  Ser  Leu  Thr  Asp  Pro  Asp  Asn
                    1395                1400                     1405

CGG  CGC  CCC  TTC  AGC  TTC  GCC  GAA  CGG  ATT  AGG  GCC  TTG  GAC  CAG  TTG         2511
Arg  Arg  Pro  Phe  Ser  Phe  Ala  Glu  Arg  Ile  Arg  Ala  Leu  Asp  Gln  Leu
               1410                1415                     1420

GAC  GCC  GGC  CAC  CGT  CCG  GAC  TCC  TTC  CAG  GAC  GAG  GCG  GTC  AAG  CTG         2559
Asp  Ala  Gly  His  Arg  Pro  Asp  Ser  Phe  Gln  Asp  Glu  Ala  Val  Lys  Leu
1425                1430                1435                     1440

CTG  GTC  ACC  TCG  AGG  GCG  CTG  CGG  CTG  CGG  CGG  AAC  CGG  CCC  GAG  CTC         2607
Leu  Val  Thr  Ser  Arg  Ala  Leu  Arg  Leu  Arg  Arg  Asn  Arg  Pro  Glu  Leu
                    1445                1450                     1455

TTC  ACC  GGC  TAC  CGC  CCC  GTG  CAT  GCC  AGG  GGC  CCC  GCC  GCC  GGG  CAC         2655
Phe  Thr  Gly  Tyr  Arg  Pro  Val  His  Ala  Arg  Gly  Pro  Ala  Ala  Gly  His
                    1460                1465                     1470

CTG  GTG  GCG  TTC  GAC  CGC  GGC  GCC  GGG  GGA  GTG  CTG  GCG  CTT  GCC  ACC         2703
Leu  Val  Ala  Phe  Asp  Arg  Gly  Ala  Gly  Gly  Val  Leu  Ala  Leu  Ala  Thr
                    1475                1480                     1485

CGG  CTC  CCC  TAC  GGG  CTG  GAA  CAG  TCG  GGC  GGC  TGG  CGG  GAC  ACC  GCC         2751
Arg  Leu  Pro  Tyr  Gly  Leu  Glu  Gln  Ser  Gly  Gly  Trp  Arg  Asp  Thr  Ala
1490                1495                     1500

GTC  GAG  CTT  GAA  GCC  GCC  ATG  ACG  GAC  GAA  CTG  ACC  GGC  TCC  ACT  TTC         2799
Val  Glu  Leu  Glu  Ala  Ala  Met  Thr  Asp  Glu  Leu  Thr  Gly  Ser  Thr  Phe
1505                1510                1515                     1520

GGG  CCG  GGA  CCG  GCG  GCG  CTG  TCA  GAA  GTC  TTC  CGG  GCC  TAC  CCG  GTG         2847
Gly  Pro  Gly  Pro  Ala  Ala  Leu  Ser  Glu  Val  Phe  Arg  Ala  Tyr  Pro  Val
                    1525                1530                     1535

GCC  TTG  TTG  GTC  CCC  GCG  ACA  GGA  GGC  AAG  TCA  TGACGCAGCC  CAACGATGCG         2900
Ala  Leu  Leu  Val  Pro  Ala  Thr  Gly  Gly  Lys  Ser
                    1540                1545

GCCAAGCCGG  TGCAGGGAGC  GGGGCGCTTC  GATATC                                             2936
```

( 2 ) INFORMATION FOR SEQ ID NO:11:

( i ) SEQUENCE CHARACTERISTICS:

( A ) LENGTH: 3073 base pairs
( B ) TYPE: nucleic acid
( C ) STRANDEDNESS: single
( D ) TOPOLOGY: linear ( i i ) MOLECULE TYPE: cDNA ( i x ) FEATURE:
(A) NAME/KEY: CDS
(B) LOCATION: 678..3002

( x i ) SEQUENCE DESCRIPTION: SEQ ID NO:11:

```
GATCCGGACG  GCAACCTCAT  GTCCCCGGAG  GACTGGGACA  GCGGCTTCGG  CCGTTCGGTG         60

GGCATGTTCC  TCAACGGCGA  CGGCATCCAG  GGCCACGATG  ACCGCGGCCG  CCGCATCACG        120

GACGTGAACT  TCCTGCTGTA  CTTCAACGCC  ACGACGGCG   ACGTCGAGTT  CACGCTGCCG        180

CCGGACGAAT  ACGCCCCGGC  CTGGGACGTC  ATCATCGACA  CCGCCGGTGA  AGGGGCCGAC        240

TCCAAGCCCG  CGGACGCCGG  AACCATCCTG  TCCGTTGCGG  CCAAGTCGCT  GGTTGTGCTT        300

CGCGCCCACA  GCGCACCGGA  GGAGGAGCCT  GACCATTCCG  TGGCTGCTTC  CCTGGCTGCA        360

CTGACGCAGA  CCGCCACCGC  CGAGACGGCG  GCGCTCACAG  CTCCTGCCGT  TCCCGAGCCG        420

GCCAAGACGA  AGAAGCCGGC  CGCTGACCCG  GTTGCTGAAC  CGGCCGACCC  GCCGGTTGCT        480

GACCCGGCCG  ACCCGGTTGC  TGACCCGGTT  GCTGACCCGG  CGCCGGAACC  GGCTGCGGAG        540

CCTGCGAAAT  CCGCAGCGGA  ACCTGGTGCG  GAGCCTGCGA  AGGACCCGGA  GGAGCAGCCG        600

GCGGAAAAGC  CGGCGCGCAA  GCCTGCGGCA  AAGCGCGGCG  CCACCTGAG   GCGGTCAAG        660

CCCGCTGGGG  AGGACGC ATG AGA ACG CCA GTC TCC ACG TAC AGG CTG CAG              710
               Met Arg Thr Pro Val Ser Thr Tyr Arg Leu Gln
                    775                 780

ATC AGG AAG GGA TTC ACA CTC TTC GAC GCG GCC AAA ACC GTT CCG TAC              758
Ile Arg Lys Gly Phe Thr Leu Phe Asp Ala Ala Lys Thr Val Pro Tyr
    785                 790                 795

CTG CAC TCG CTC GGC GTC GAC TGG GTC TAC CTT TCT CCG GTC CTG ACT              806
Leu His Ser Leu Gly Val Asp Trp Val Tyr Leu Ser Pro Val Leu Thr
800                 805                 810                 815

GCC GAG CAG GGC TCC GAC CAC GGG TAC GAC GTC ACC GAT CCC TCC GCC              854
Ala Glu Gln Gly Ser Asp His Gly Tyr Asp Val Thr Asp Pro Ser Ala
                820                 825                 830

GTC GAC CCC GAA CGC GGC GGG CCG GAG GGC CTC GCG GCG GTT TCC AAG              902
Val Asp Pro Glu Arg Gly Gly Pro Glu Gly Leu Ala Ala Val Ser Lys
            835                 840                 845

GCG GCC CGC GCC GCG GGC ATG GGC GTG CTG ATC GAC ATC GTG CCC AAC              950
Ala Ala Arg Ala Ala Gly Met Gly Val Leu Ile Asp Ile Val Pro Asn
        850                 855                 860

CAC GTG GGC GTC GCG ACG CCG GCG CAG AAC CCC TGG TGG TGG TCG CTG              998
His Val Gly Val Ala Thr Pro Ala Gln Asn Pro Trp Trp Trp Ser Leu
    865                 870                 875

CTC AAG GAG GGA CGC CAG TCC CGT TAC GCG GAG GCG TTC GAC GTC GAT             1046
Leu Lys Glu Gly Arg Gln Ser Arg Tyr Ala Glu Ala Phe Asp Val Asp
880                 885                 890                 895

TGG GAC CTC GCC GGG GGA CGC ATC CGG CTG CCG GTG CTC GGC AGC GAC             1094
Trp Asp Leu Ala Gly Gly Arg Ile Arg Leu Pro Val Leu Gly Ser Asp
                900                 905                 910

GAT GAC CTC GAC CAG CTC GAA ATC AGG GAC GGG GAG CTG CGG TAC TAC             1142
Asp Asp Leu Asp Gln Leu Glu Ile Arg Asp Gly Glu Leu Arg Tyr Tyr
            915                 920                 925

GAC CAC CGA TTC CCG CTC GCC GAG GGA ACC TAC GCC GAA GGC GAC GCC             1190
Asp His Arg Phe Pro Leu Ala Glu Gly Thr Tyr Ala Glu Gly Asp Ala
        930                 935                 940

CCG CGG GAT GTC CAC GCC CGG CAG CAC TAC GAG CTC ATC GGC TGG CGC             1238
```

```
        Pro Arg Asp Val His Ala Arg Gln His Tyr Glu Leu Ile Gly Trp Arg
        945                 950                 955

CGC GCG GAC AAC GAG CTG AAC TAC CGC CGC TTT TTC GCG GTG AAC ACG        1286
Arg Ala Asp Asn Glu Leu Asn Tyr Arg Arg Phe Phe Ala Val Asn Thr
960                 965                 970                 975

CTC GCC GGC GTC CGC GTG GAA ATC CCC GCC GTC TTC GAC GAG GCA CAC        1334
Leu Ala Gly Val Arg Val Glu Ile Pro Ala Val Phe Asp Glu Ala His
                    980                 985                 990

CAG GAG GTG GTG CGC TGG TTC CGC GAG GAC CTT GCG GAC GGC CTG CGG        1382
Gln Glu Val Val Arg Trp Phe Arg Glu Asp Leu Ala Asp Gly Leu Arg
                995                 1000                1005

ATC GAC CAC CCG GAC GGC CTC GCT GAC CCC GAG GGG TAC CTG AAG CGA        1430
Ile Asp His Pro Asp Gly Leu Ala Asp Pro Glu Gly Tyr Leu Lys Arg
            1010                1015                1020

CTC CGG GAA GTC ACC GGC GGC GCT TAC CTG CTG ATC GAA AAG ATC CTG        1478
Leu Arg Glu Val Thr Gly Gly Ala Tyr Leu Leu Ile Glu Lys Ile Leu
1025                1030                1035

GAG CCG GGG GAG CAG CTG CCC GCC AGC TTC GAG TGT GAA GGC ACC ACA        1526
Glu Pro Gly Glu Gln Leu Pro Ala Ser Phe Glu Cys Glu Gly Thr Thr
1040                1045                1050                1055

GGC TAC GAC GCC CTC GCC GAC GTC GAC CGG GTT CTC GTG GAC CCG CGC        1574
Gly Tyr Asp Ala Leu Ala Asp Val Asp Arg Val Leu Val Asp Pro Arg
                1060                1065                1070

GGC CAG GAA CCG CTG GAC CGG CTT GAC GCG TCC CTG CGT GGC GGC GAG        1622
Gly Gln Glu Pro Leu Asp Arg Leu Asp Ala Ser Leu Arg Gly Gly Glu
            1075                1080                1085

CCC GCC GAC TAC CAG GAC ATG ATC CGC GGA ACC AAG CGC CGG ATC ACC        1670
Pro Ala Asp Tyr Gln Asp Met Ile Arg Gly Thr Lys Arg Arg Ile Thr
        1090                1095                1100

GAC GGT ATC CTG CAC TCG GAG ATC CTG CGG CTG GCC CGG CTG GTT CCG        1718
Asp Gly Ile Leu His Ser Glu Ile Leu Arg Leu Ala Arg Leu Val Pro
1105                1110                1115

GGC GAC GCC AAC GTT TCA ATC GAC GCC GGA GCC GAC GCT CTC GCC GAA        1766
Gly Asp Ala Asn Val Ser Ile Asp Ala Gly Ala Asp Ala Leu Ala Glu
1120                1125                1130                1135

ATC ATC GCC GCC TTC CCG GTC TAC CGC ACC TAC CTG CCG GAG GGC GCC        1814
Ile Ile Ala Ala Phe Pro Val Tyr Arg Thr Tyr Leu Pro Glu Gly Ala
                1140                1145                1150

GAG GTC CTG AAG GAG GCG TGC GAG CTT GCC GCG CGT AGG CGG CCG GAA        1862
Glu Val Leu Lys Glu Ala Cys Glu Leu Ala Ala Arg Arg Arg Pro Glu
            1155                1160                1165

CTC GAC CAG GCC ATC CAG GCT CTG CAG CCG CTG CTG CTG GAC ACG GAC        1910
Leu Asp Gln Ala Ile Gln Ala Leu Gln Pro Leu Leu Leu Asp Thr Asp
        1170                1175                1180

CTC GAG CTT GCC CGG CGC TTC CAG CAG ACC TCG GGC ATG GTC ATG GCC        1958
Leu Glu Leu Ala Arg Arg Phe Gln Gln Thr Ser Gly Met Val Met Ala
1185                1190                1195

AAG GGC GTG GAG GAC ACC GCG TTC TTC CGC TAC AAC CGC CTG GGC ACC        2006
Lys Gly Val Glu Asp Thr Ala Phe Phe Arg Tyr Asn Arg Leu Gly Thr
1200                1205                1210                1215

CTC ACG GAA GTG GGC GCC GAC CCC ACC GAG TTC GCC GTG GAG CCG GAC        2054
Leu Thr Glu Val Gly Ala Asp Pro Thr Glu Phe Ala Val Glu Pro Asp
                1220                1225                1230

GAG TTC CAC GCC CGG CTG GCA CGC CGG CAG GCC GAG CTT CCG CTG TCC        2102
Glu Phe His Ala Arg Leu Ala Arg Arg Gln Ala Glu Leu Pro Leu Ser
            1235                1240                1245

ATG ACG ACG CTG AGC ACG CAC GAC ACC AAG CGC AGC GAG GAC ACC CGA        2150
Met Thr Thr Leu Ser Thr His Asp Thr Lys Arg Ser Glu Asp Thr Arg
        1250                1255                1260

GCA AGG ATT TCG GTC ATT TCC GAG GTT GCG GGT GAC TGG AAA AAG GCC        2198
```

```
Ala  Arg  Ile  Ser  Val  Ile  Ser  Glu  Val  Ala  Gly  Asp  Trp  Glu  Lys  Ala
     1265                1270                     1275

TTG  AAC  CGG  CTG  CGC  GAC  CTG  GCC  CCG  CTG  CCG  GAC  GGC  CCG  CTG  TCC        2246
Leu  Asn  Arg  Leu  Arg  Asp  Leu  Ala  Pro  Leu  Pro  Asp  Gly  Pro  Leu  Ser
1280                1285                     1290                     1295

GCG  CTG  CTC  TGG  CAG  GCC  ATT  GCC  GGC  GCC  TGG  CCC  GCC  AGC  CGG  GAA        2294
Ala  Leu  Leu  Trp  Gln  Ala  Ile  Ala  Gly  Ala  Trp  Pro  Ala  Ser  Arg  Glu
                    1300                    1305                     1310

CGC  CTG  CAG  TAC  TAC  GCG  CTG  AAG  GCC  GCG  CGT  GAA  GCG  GGG  AAC  TCG        2342
Arg  Leu  Gln  Tyr  Tyr  Ala  Leu  Lys  Ala  Ala  Arg  Glu  Ala  Gly  Asn  Ser
                    1315                    1320                     1325

ACC  AAC  TGG  ACC  GAT  CCG  GCC  CCC  GCG  TTC  GAG  GAG  AAG  CTG  AAG  GCC        2390
Thr  Asn  Trp  Thr  Asp  Pro  Ala  Pro  Ala  Phe  Glu  Glu  Lys  Leu  Lys  Ala
               1330                    1335                1340

GCG  GTC  GAC  GCC  GTG  TTC  GAC  AAT  CCC  GCC  GTG  CAG  GCC  GAG  GTG  GAA        2438
Ala  Val  Asp  Ala  Val  Phe  Asp  Asn  Pro  Ala  Val  Gln  Ala  Glu  Val  Glu
          1345                    1350                    1355

GCC  CTC  GTC  GAG  CTC  CTG  GAG  CCG  TAC  GGA  GCT  TCG  AAC  TCC  CTC  GCC        2486
Ala  Leu  Val  Glu  Leu  Leu  Glu  Pro  Tyr  Gly  Ala  Ser  Asn  Ser  Leu  Ala
1360                1365                     1370                    1375

GCC  AAG  CTC  GTG  CAG  CTG  ACC  ATG  CCC  GGC  GTC  CCG  GAC  GTC  TAC  CAG        2534
Ala  Lys  Leu  Val  Gln  Leu  Thr  Met  Pro  Gly  Val  Pro  Asp  Val  Tyr  Gln
                    1380                    1385                    1390

GGC  ACG  GAG  TTC  TGG  GAC  CGG  TCG  CTG  ACG  GAC  CCG  GAC  AAC  CGG  CGG        2582
Gly  Thr  Glu  Phe  Trp  Asp  Arg  Ser  Leu  Thr  Asp  Pro  Asp  Asn  Arg  Arg
                    1395                    1400                    1405

CCG  TTC  AGC  TTC  GAC  GAC  CGC  CGC  GCC  GCG  CTG  GAG  CAG  CTG  GAT  GCC        2630
Pro  Phe  Ser  Phe  Asp  Asp  Arg  Arg  Ala  Ala  Leu  Glu  Gln  Leu  Asp  Ala
               1410                    1415                    1420

GGC  GAC  CTT  CCC  GCG  TCA  TTT  ACC  GAT  GAG  CGG  ACG  AAG  CTG  CTA  GTG        2678
Gly  Asp  Leu  Pro  Ala  Ser  Phe  Thr  Asp  Glu  Arg  Thr  Lys  Leu  Leu  Val
          1425                    1430                    1435

ACG  TCG  CGC  GCG  CTG  CGG  CTG  CGC  CGG  GAC  CGT  CCG  GAG  CTG  TTC  ACG        2726
Thr  Ser  Arg  Ala  Leu  Arg  Leu  Arg  Arg  Asp  Arg  Pro  Glu  Leu  Phe  Thr
1440                1445                    1450                    1455

GGG  TAC  CGG  CCG  GTC  CTG  GCC  AGC  GGG  CCC  GCC  GCC  GGG  CAC  CTG  CTC        2774
Gly  Tyr  Arg  Pro  Val  Leu  Ala  Ser  Gly  Pro  Ala  Ala  Gly  His  Leu  Leu
                    1460                    1465                    1470

GCG  TTC  GAC  CGC  GGC  ACC  GCG  GCG  GCG  CCG  GGT  GCA  TTG  ACC  CTC  GCC        2822
Ala  Phe  Asp  Arg  Gly  Thr  Ala  Ala  Ala  Pro  Gly  Ala  Leu  Thr  Leu  Ala
               1475                    1480                    1485

ACG  CGG  CTT  CCC  TAC  GGG  CTG  GAA  CAG  TCG  GGT  GGA  TGG  CGG  GAC  ACC        2870
Thr  Arg  Leu  Pro  Tyr  Gly  Leu  Glu  Gln  Ser  Gly  Gly  Trp  Arg  Asp  Thr
               1490                    1495                    1500

GCC  GTC  GAA  CTT  AAC  ACC  GCC  ATG  AAA  GAC  GAA  CTG  ACC  GGT  GCC  GGC        2918
Ala  Val  Glu  Leu  Asn  Thr  Ala  Met  Lys  Asp  Glu  Leu  Thr  Gly  Ala  Gly
          1505                    1510                    1515

TTC  GGA  CCG  GGG  GCA  GTG  AAG  ATC  GCC  GAC  ATC  TTC  CGG  TCG  TTC  CCC        2966
Phe  Gly  Pro  Gly  Ala  Val  Lys  Ile  Ala  Asp  Ile  Phe  Arg  Ser  Phe  Pro
1520                1525                    1530                    1535

GTT  GCG  CTG  CTG  GTG  CCG  CAG  ACA  GGA  GGA  GAG  TCA  TGACGCACAC                3012
Val  Ala  Leu  Leu  Val  Pro  Gln  Thr  Gly  Gly  Glu  Ser
                    1540                    1545

CTACCCGCGG  GAAGCCGCGA  AACCCGTCCT  GGGCCCCGCA  CGCTACGACG  TCTGGGCGCC              3072

C                                                                                    3073
```

( 2 ) INFORMATION FOR SEQ ID NO:12:

( i ) SEQUENCE CHARACTERISTICS:
        ( A ) LENGTH: 20 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

Met Arg Thr Pro Ala Ser Thr Tyr Arg Leu Gln Ile Arg Arg Gly Phe
1               5                   10                  15
Thr Leu Phe Asp
            20

(2) INFORMATION FOR SEQ ID NO:13:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:13:

Met Arg Thr Pro Val Ser Thr Tyr Arg Leu Gln Ile Arg Lys Gly Phe
1               5                   10                  15
Thr Leu Phe Asp
            20

(2) INFORMATION FOR SEQ ID NO:14:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:14:

Arg Ser Glu Asp Thr Arg Ala Arg Ile Ser Val Ile Ala Glu Val Ala
1               5                   10                  15
Pro Glu Trp Glu Lys
            20

(2) INFORMATION FOR SEQ ID NO:15:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:15:

Leu Val Gln Leu Thr Met Pro Gly Val Pro Asp Val Tyr Gln Gly Thr
1               5                   10                  15
Glu Phe Trp Asp Arg
            20

(2) INFORMATION FOR SEQ ID NO:16:

(i) SEQUENCE CHARACTERISTICS:
    (A) LENGTH: 20 amino acids
    (B) TYPE: amino acid
    (C) STRANDEDNESS: single
    (D) TOPOLOGY: linear -continued (ii) MOLECULE TYPE: peptide (xi) SEQUENCE DESCRIPTION: SEQ ID NO:16:

```
Leu Val Gln Leu Thr Met Pro Gly Val Pro Asp Val Tyr Gln Gly Thr
1               5                   10                  15
Glu Phe Trp Asp
            20
```

(2) INFORMATION FOR SEQ ID NO:17:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:17:

```
Glu Gly Arg Gln Ser Arg Tyr Ala Glu Ala Phe Asp Val Asp Trp Asp
1               5                   10                  15
Leu Ala Gly Gly
            20
```

DNA ENCODING ENZYME RECOMBINANT DNA AND ENZYME TRANSFORMANT, AND THEIR PREPARATION AND USES

CROSS-REFERENCE TO RELATED APPLICATIONS

The present application is a division of copending parent application Ser. No. 08/393,540, filed Feb. 23, 1995.

BACKGROUND OF THE INVENTION

1. Field of the Invention

The present invention relates to a novel DNA encoding an enzyme which forms non-reducing saccharides having trehalose structure as an end unit from reducing amylaceous saccharides having a degree of glucose polymerization of 3 or higher, and a recombinant DNA and enzyme containing the DNA as well as to a transformant. The present invention further relates to preparations and uses thereof.

2. Description of the Prior Art

Trehalose is a disaccharide which consists of 2 glucose molecules that are linked together with their reducing groups, and, naturally, it is present in fungi, algae, insects, etc., in an extremely small quantity. Having no reducing residue within the molecule, trehalose does not cause an unsatisfactory browning reaction even when heated in the presence of amino acids or the like, and because of this it can sweeten food products without fear of causing unsatisfiable coloration and deterioration. Trehalose, however, is far from being readily prepared in a desired amount by conventional production methods, and, actually, it has scarcely been used for sweetening food products.

Conventional production methods are roughly classified into 2 groups, i.e. the one using cells of microorganisms and the other employing a multi-enzymatic system wherein enzymes are allowed to act on saccharides. The former, as disclosed in Japanese Patent Laid-Open No. 154,485/75, is a method comprising growing microorganisms such as bacteria and yeasts in nutrient culture media, and collecting trehalose from the proliferated cells in the resultant cultures. The latter, as disclosed in Japanese Patent Laid-Open No. 216,695/83, is a method comprising providing maltose as a substrate, allowing a multi-enzymatic system using maltose- and trehalose-phosphorylases to act on maltose, and recovering the formed trehalose from the reaction system. Although the former facilitates the growth of microorganisms with relative ease, it requires sequential complicated steps for collecting trehalose from the microorganisms containing only 15 w/w % trehalose, on a dry solid basis (d.s.b.). While the latter enables to separate trehalose with relative ease, but it is theoretically difficult to increase the trehalose yield by allowing enzymes to act on substrates at a considerably-high concentration because the enzymatic reaction in itself is an equilibrium reaction of 2 different types of enzymes and the equilibrium point constantly inclines to the side of forming glucose phosphate.

In view of the foregoing, the present inventors energetically screened enzymes which form saccharides having trehalose structure from amylaceous saccharides, and found that microorganisms such as those of the species *Rhizobium sp.* M-11 and *Arthrobacter sp.* Q36 produce a novel enzyme which forms non-reducing saccharides having trehalose structure as an end unit from reducing amylaceous saccharides having a degree of glucose polymerization of 3 or higher. Before or after this finding, it was revealed that such a non-reducing saccharide is almost quantitatively hydrolyzed into trehalose and glucose and/or maltooligosaccharides by another enzyme produced by the same microorganisms as mentioned above. Since the use of the combination of enzymes enables to form a desired amount of trehalose with relative ease, the aforementioned objects relating to trehalose would be completely overcome. Insufficient levels of production of the novel enzyme by such a microorganism is a drawback, i.e. a relatively-large scale culture thereof is inevitably used to industrially produce trehalose and/or non-reducing saccharides having trehalose structure as an end unit.

Recombinant DNA technology has made a remarkable progress in recent years. At present, even an enzyme whose total amino acid sequence has not been revealed can be readily prepared in a desired amount, if a gene encoding the enzyme was once isolated and the base sequence was decoded, by preparing a recombinant DNA which contains a DNA encoding the enzyme, introducing the recombinant DNA into microorganisms or cells of plants and animals, and culturing the resultant transformants. There is a pressing need to find a gene encoding the enzyme and to reveal a base sequence thereof.

SUMMARY OF THE INVENTION

It is an object of the present invention to provide a DNA encoding an enzyme which forms non-reducing saccharides having trehalose structure as an end unit from reducing amylaceous saccharides having a degree of glucose polymerization of 3 or higher.

It is a further object of the present invention to provide a recombinant DNA which contains the DNA and a self-replicable vector.

It is yet another object of the present invention to provide a recombinant enzyme, which forms non-reducing saccharides having trehalose structure as an end unit from reducing amylaceous saccharides having a degree of glucose polymerization of 3 or higher, by means of recombinant DNA technology.

It is another object of the present invention to provide a transformant obtainable by introducing the recombinant DNA into a suitable host.

It is a further object of the present invention to provide a preparation of the recombinant enzyme.

It is yet another object of the present invention to provide a method to convert reducing amylaceous saccharides by using the recombinant enzyme.

The first object of the present invention is attained by a DNA encoding an enzyme which forms non-reducing saccharides having trehalose structure as an end unit from reducing amylaceous saccharides having a degree of glucose polymerization of 3 or higher.

The second object of the present invention is attained by a replicable recombinant DNA which contains a self-replicable vector and a DNA which encodes a non-reducing saccharide-forming enzyme.

The third object of the present invention is attained by a recombinant enzyme which forms non-reducing saccharides having trehalose structure as an end unit from reducing amylaceous saccharides having a degree of glucose polymerization of 3 or higher.

The fourth object of the present invention is attained by a transformant into which a replicable recombinant DNA containing a self-replicable vector and a DNA encoding an enzyme which forms non-reducing saccharides having trehalose structure as an end unit from reducing amylaceous saccharides having a degree of glucose polymerization of 3 or higher.

The fifth object of the present invention is attained by a process for producing a recombinant enzyme, which contains a step of culturing a transformant capable of forming the recombinant enzyme, and collecting the enzyme from the resultant culture.

The sixth object of the present invention is attained by a method for converting reducing amylaceous saccharides, which contains a step of allowing the recombinant enzyme to act on reducing amylaceous saccharides having a degree of glucose polymerization of 3 or higher to form from them non-reducing saccharides having trehalose structure as an end unit.

BRIEF DESCRIPTION OF THE ACCOMPANYING DRAWINGS

DETAILED DESCRIPTION OF THE INVENTION

Figure 1:
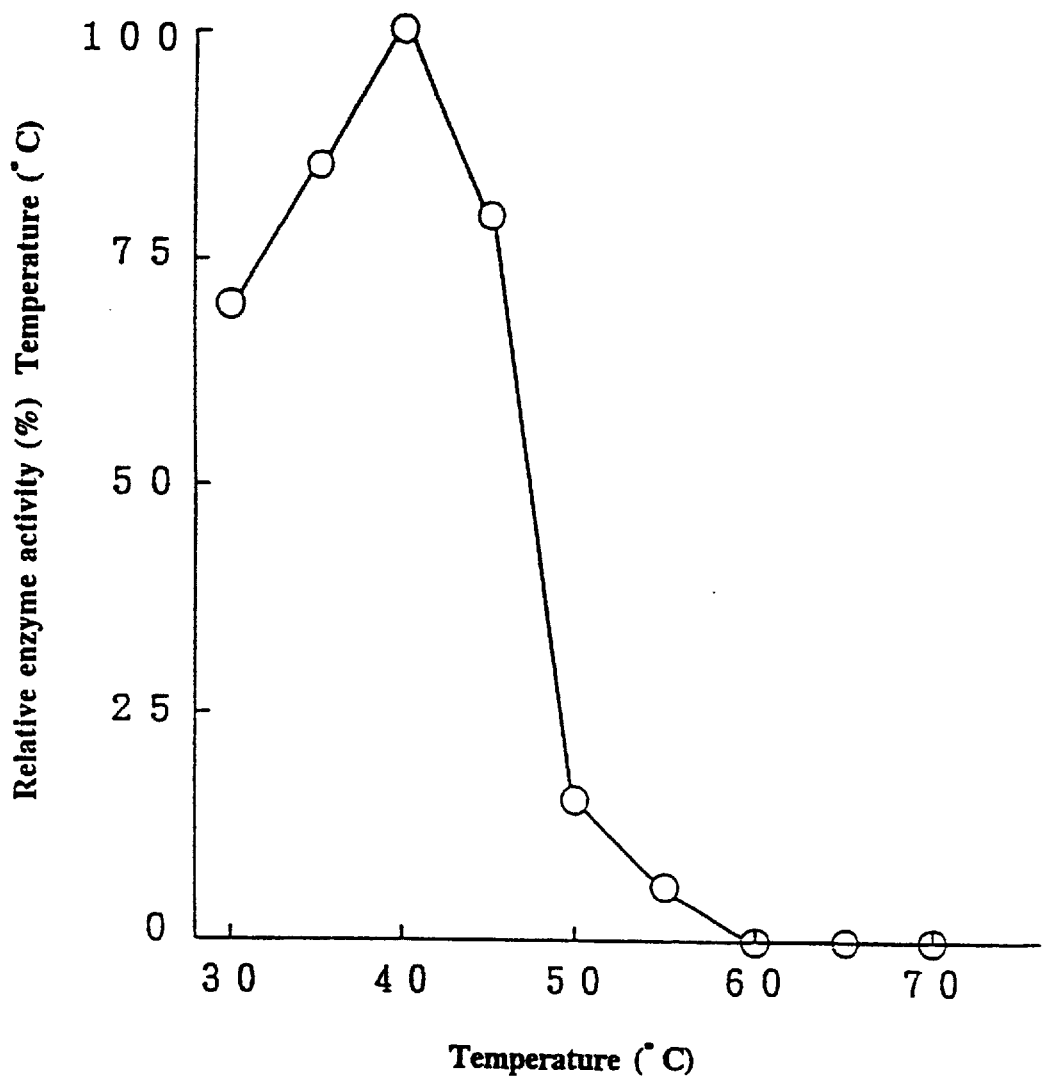
FIG. 1 shows the optimum temperature of enzyme M-11.

The DNA according to the present invention exerts the production of the non-reducing saccharide-forming enzyme encoded by the DNA in a manner that the DNA is inserted into an appropriate self-replicable vector to form a replicable recombinant DNA, followed by introducing the recombinant DNA into a host, which is incapable of producing the enzyme but readily replicable, to form a transformant.

Although the recombinant DNA per se does not produce the enzyme, the production of the enzyme encoded by the DNA is induced by introducing the recombinant DNA into a host, which is incapable of producing the enzyme but replicable with relative ease, to form a transformant, and culturing the transformant to produce the enzyme.

The transformant according to the present invention produces the enzyme when cultured.

The recombinant enzyme according to the present invention acts on reducing amylaceous saccharides having a degree of glucose polymerization of 3 or higher to form non-reducing saccharides having trehalose structure as an end unit.

The culture of the transformant according to the present invention yields a desired amount of the enzyme with relative ease.

The conversion method according to the present invention converts reducing amylaceous saccharides having a degree of glucose polymerization of 3 or higher into non-reducing saccharides having trehalose structure as an end unit.

The present invention was made based on the finding of a novel enzyme which forms non-reducing saccharides having trehalose structure as an end unit from reducing amylaceous saccharides having a degree of glucose polymerization of 3 or higher. The enzyme can be obtained from cultures of microorganisms of the species *Rhizobium sp.* M-11 and *Arthrobacter sp.* Q36 (the enzymes from *Rhizobium sp.* M-11 and *Arthrobacter sp.* Q36 are respectively designated as "enzyme M-11" and "enzyme Q36" hereinafter), and the present inventors isolated the enzyme using a combination of conventional purification methods which mainly includes column chromatography, and examined the properties and features to reveal a polypeptide having the following physicochemical properties:

(1) Action
   Forming non-reducing saccharides having trehalose structure as an end unit from reducing saccharides having a degree of glucose polymerization of 3 or higher;

(2) Molecular weight
   About 76,000–87,000 daltons on sodium dodecyl sulfate polyacrylamide gel electrophoresis (SDS-PAGE);

(3) Isoelectric point
   About 3.6–4.6 on isoelectrophoresis;

(4) Optimum temperature
   Exhibiting an optimum temperature of around 35°–40° C. when incubated at pH 7.0 for 60 min;

(5) Optimum pH
   Exhibiting an optimum pH of around 6.4–7.2 when incubated at 40° C. for 60 min;

(6) Thermal stability
   Stable up to a temperature of around 35°–40° C. when incubated at pH 7.0 for 60 min; and (7) pH Stability
   Stable up to a pH of around 5.5–11.0 when incubated at 25° C. for 16 hours.

The experiments, which were conducted to reveal the aforesaid physicochemical properties, are explained in the below:

EXPERIMENT 1

Preparation of purified enzyme

Experiment 1-1

Preparation of enzyme derived from Rhizobium sp. M-11

In 500-ml Erlenmeyer flasks were placed 100 ml aliquots of a liquid culture medium (pH 7.0) containing 2.0 w/v % maltose, 0.5 w/v % peptone, 0.1 w/v % yeast extract, 0.1 w/v % disodium hydrogen phosphate, and 0.1 w/v % potassium dihydrogen phosphate, and the flasks were autoclaved at 120° C. for 20 min to effect sterilization. After cooling the flasks a seed culture of *Rhizobium sp.* M-11 was inoculated into each liquid culture medium in each flask, followed by the incubation at 27° C. for 24 hours under rotary-shaking conditions. Twenty L of a fresh preparation of the same liquid culture medium was put in a 30-L jar fermentor and sterilized, followed by inoculating one v/v % of the culture obtained in the above into the sterilized liquid culture medium in the jar fermentor, and incubating it at a pH of 6–8 and 30° C. for 24 hours under aeration and agitation conditions.

Thereafter, about 18 L of the resultant culture was subjected to an ultra-high pressure cell disrupting apparatus to disrupt cells, and the resultant suspension was centrifuged to obtain a supernatant, and to about 16 L of which was added ammonium sulfate to give a 20 w/v % saturation, allowed to stand at 4° C. for one hour, and centrifuged to remove sediment. To the resultant supernatant was added ammonium sulfate to give a 60 w/v % saturation, allowed to stand at 4° C. for 24 hours, and centrifuged to collect sediment which was then dissolved in a minimum amount of 10 mM phosphate buffer (pH 7.0). The resultant solution was dialyzed against 10 mM phosphate buffer (pH 7.0) for 24 hours, and centrifuged to remove insoluble substances. The supernatant thus obtained was fed to a column packed with "DEAE-TOYOPEARL®", a product for ion-exchange chromatography commercialized by Tosoh Corporation, Tokyo, Japan, which had been previously equilibrated with 10 mM phosphate buffer (pH 7.0), followed by feeding to the column a linear gradient buffer of sodium chloride ranging from 0M to 0.5M in 10 mM phosphate buffer (pH 7.0). Fractions containing the objective enzyme were collected from the eluate, pooled, dialyzed for 10 hours against 50 mM phosphate buffer (pH 7.0) containing 2M ammonium sulfate, and centrifuged to remove insoluble substances. Thereafter, the resultant supernatant was fed to a column, which had been packed with "BUTYL TOYOPEARL®", a gel for hydrophobic column chromatography commercialized by Tosoh Corporation, Tokyo, Japan, and equilibrated with 50 mM phosphate buffer (pH 7.0) containing 2M ammonium sulfate, followed by feeding to the column a linear gradient buffer of ammonium sulfate ranging from 2M to 0M in 50 mM phosphate buffer (pH 7.0). Fractions containing the objective enzyme were collected from the eluate, pooled, fed to a column packed with "TOYOPEARL® HW-55", a product for gel filtration column chromatography commercialized by Tosoh Corporation, Tokyo, Japan, which had been previously equilibrated with 50 mM phosphate buffer (pH 7.0), followed by feeding to the column 50 mM phosphate buffer (pH 7.0) and collecting fractions containing the objective enzyme. The enzyme thus obtained had a specific activity of about 195 units/mg protein, and the yield was about 220 units per L of the culture.

Throughout the specification the enzyme activity is expressed by the value measured on the following assay: Placing 4 ml of 50 mM phosphate buffer (pH 7.0) containing 1.25 w/v % maltopentaose in a test tube, add one ml of an enzyme solution to the tube, and incubate the resultant solution at 40° C. for 60 min to effect enzymatic reaction. Thereafter, heating the resultant reaction mixture at 100° C. for 10 min to suspend the enzymatic reaction. Diluting the resultant reaction mixture with distilled water by 10 times, and assay the reducing activity on the Somogyi-Nelson's method. One unit activity of the enzyme is defined as the amount of enzyme which reduces the reducing power corresponding to one $\mu$mol maltopentaose per min tinder the same conditions as described above.

Experiment 1-2
Purification of enzyme Q36

Similarly as in Experiment 1-1, a seed culture of *Arthrobacter sp.*Q36 was cultured, and the resultant culture was treated to obtain a purified enzyme Q36 having a specific activity of about 200 units/mg protein in a yield of about 295 units per L of the culture.

EXPERIMENT 2
Physicochemical property of enzyme

Experiment 2-1
Action

To 50 mM phosphate buffer (pH 7.0) containing 20 w/v % of glucose, maltose, maltotriose, maltotetraose, maltopentaose, maltohexaose or maltoheptaose as a substrate was added 2 units/g substrate, d.s.b., of the purified enzyme M-11 or enzyme Q36 obtained in Experiment 1, and the mixture was enzymatically reacted at 40° C. for 48 hours. The reaction mixture was desalted in usual manner, fed to "WB-T-330", a column for high-performance liquid chromatography (HPLC) commercialized by Tosoh Corporation, Tokyo, Japan, followed by feeding to the column distilled water at a flow rate of 0.5 ml/min at ambient temperature to separate saccharides contained in the reaction mixture while monitoring the saccharide concentration of the eluate with "MODEL RI-8012", a differential refractometer commercialized by Wako Pure Chemical Industries, Ltd., Tokyo, Japan. The saccharide composition of the reaction mixture was given in Table 1 or 2. In the table, the symbols "P1" to "P5" were named for the formed saccharides in the order from the smallest one to the largest one in terms of their degrees of glucose polymerization.

TABLE 1

| Substrate | Saccharide in reaction mixture | Elution time (min) | Composition (%) |
|---|---|---|---|
| Glucose | Glucose | 33.4 | 100.0 |
| Maltose | Maltose | 28.5 | 100.0 |
| Maltotriose | P1 + | 23.3 | 35.0 |
|  | Maltotriose | 25.9 | 65.0 |
| Maltotetraose | P2 + | 21.6 | 85.6 |
|  | Maltotetraose | 24.1 | 14.4 |
| Maltopentaose | P3 + | 19.7 | 92.7 |
|  | Maltopentaose | 22.6 | 7.3 |
| Maltohexaose | P4 + | 18.7 | 93.5 |
|  | Maltohexaose | 21.4 | 6.5 |
| Maltoheptaose | P5 + | 17.8 | 93.4 |
|  | Maltoheptaose | 21.0 | 6.7 |

TABLE 2

| Substrate | Saccharide in reaction mixture | Elution time (min) | Composition (%) |
|---|---|---|---|
| Glucose | Glucose | 33.4 | 100.0 |
| Maltose | Maltose | 28.5 | 100.0 |
| Maltotriose | P1 + | 23.3 | 35.5 |
|  | Maltotriose | 25.9 | 64.5 |
| Maltotetraose | P2 + | 21.6 | 85.8 |
|  | Maltotetraose | 24.1 | 14.2 |
| Maltopentaose | P3 + | 19.7 | 92.9 |
|  | Maltopentaose | 22.6 | 7.1 |
| Maltohexaose | P4 + | 18.7 | 93.2 |
|  | Maltohexaose | 21.4 | 6.7 |
| Maltoheptaose | P5 + | 17.8 | 93.1 |
|  | Maltoheptaose | 21.0 | 6.9 |

As is evident from the results in Table 1 and 2, the enzymes M-11 and Q36 newly formed saccharides from reducing saccharides having a degree of glucose polymerization of 3 or higher such as maltotriose, maltotetraose, maltopentaose, maltohexaose and maltoheptaose, but not from those having a degree of glucose polymerization less than 3 such as glucose and maltose. In the enzymatic reaction, the newly formed saccharides were P1 to P5, and the total yield of the saccharides P2 to P5 was as high as 85 w/w % or more, d.s.b.

To separate the saccharides P1 to P5, 3 jacketed stainless steel columns, having an inner diameter of 2.0 cm and a length of one m, were packed with "XT-1016, Na$^+$", a strong-acid cation exchange resin commercialized by Tokyo Organic Chemical Industries, Ltd., Tokyo, Japan, and cascaded in series. The reaction mixture containing any one of saccharides P1 to P5 was separatory applied to the columns at an inner column temperature of 55° C., followed by applying to the columns with 55° C. distilled water at a flow rate of SV (space velocity) 0.13. After examining the saccharide composition of the resultant eluate, a fraction containing 97 w/w % or more, d.s.b., of any one of saccharides P1 to P5 was recovered and pulverized in vacuo. No substantial reducing power was detected in the purified saccharides P1 to P5 on the Somogyi-Nelson's method.

To identify the saccharides P1 to P5, 50 mg one of which was weighed, dissolved in one ml of 50 mM acetate buffer (pH 4.5), and mixed with one unit of glucoamylase, followed by incubating the mixture at 40° C. for 6 hours. High-performance liquid chromatography analysis on the resultant reaction mixture detected glucose and trehalose as shown in Tables 3 and 4. When the saccharides P1 to P5 were subjected to the action of β-amylase, the saccharides P1 and P2 were not hydrolyzed by β-amylase, but the saccharides P3, P4 and P5 were respectively hydrolyzed into one mole of maltose, P2 and one mole of maltose, and P1 and 2 moles of maltose.

TABLE 3

| Substrate | Glucose (%) | Trehalose (%) | Molar ratio* |
| --- | --- | --- | --- |
| P1 | 36.2 | 63.8 | 1.07 |
| P2 | 52.0 | 48.0 | 2.06 |
| P3 | 61.4 | 38.6 | 3.02 |
| P4 | 68.3 | 31.7 | 4.09 |
| P5 | 72.9 | 27.1 | 5.11 |

Note
The molar ratios as indicated with the symbol "*" are values calculated as moles of glucose against one mole of trehalose.

TABLE 4

| Substrate | Glucose (%) | Trehalose (%) | Molar ratio* |
| --- | --- | --- | --- |
| P1 | 36.0 | 64.0 | 1.07 |
| P2 | 51.5 | 48.5 | 2.02 |
| P3 | 61.6 | 38.4 | 3.05 |
| P4 | 68.1 | 31.9 | 4.06 |
| P5 | 72.5 | 27.5 | 5.01 |

Note
The molar ratios as indicated with the symbol "*" are values calculated as moles of glucose against one mole of trehalose.

The results in Tables 3 and 4 strongly show that the saccharides P1 to P5 consist of one mole of trehalose and 1 to 5 moles of glucose. Because of the facts that glucoamylase specifically hydrolyzes the α-1,4 and α-1,6 linkages in maltooligosaccharides and that β-amylase hydrolyzes the α-1,4 linkage in maltooligosaccharides from their end terminals by maltose units, it is estimated that the saccharides P1 to P5 have a structure consisting of glucose or maltooligosaccharide having a degree of glucose polymerization of 2 to 5, both of which have a trehalose residue at their end terminals.

The total analysis of the above results identifies the saccharides P1 to P5 as α-glucosyl trehalose, α-maltosyl trehalose, α-maltotriosyl trehalose, α-maltotetraosyl trehalose and α-maltopentaosyl trehalose respectively, and this demonstrated that the enzymes have an activity of forming non-reducing saccharides having trehalose structure as an end unit from reducing saccharides having a degree of glucose polymerization of 3 or higher.

Experiment 2-2
Molecular weight
In accordance with the method reported by U. K. Laemmli in *Nature*, Vol.227, pp.680–685 (1970), the purified enzymes M-11 and Q36 in Experiment 1 were respectively electrophoresed on sodium dodecyl polyacrylamide gel electrophoresis to give a single protein band at a position corresponding to about 76,000–87,000 daltons. The marker proteins used in this experiment were myosin (MW=200,000 daltons), β-galactosidase (MW=116,250 daltons), phosphorylase B (MW=97,400 daltons), serum albumin (MW= 66,200 daltons) and ovalbumin (MW=45,000 daltons).

Experiment 2-3
Isoelectric point
The purified enzymes M-11 and Q36 obtained in Experiment 1 gave an isoelectric point of about 3.6–4.6 on isoelectrophoresis respectively.

Figure 2:
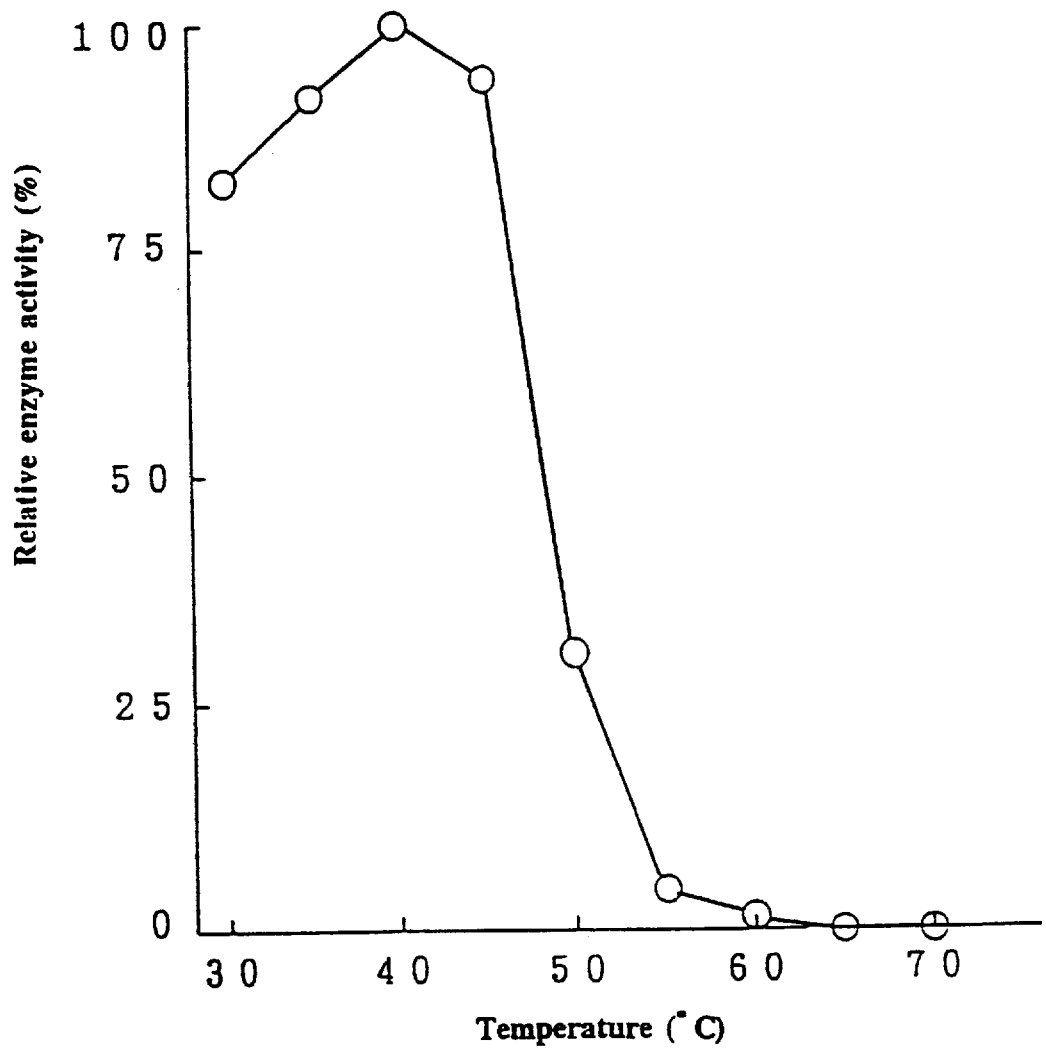
FIG. 2 shows the optimum temperature of enzyme Q36.

Experiment 2-4
Optimum temperature
The optimum temperature of the purified enzymes M-11 and Q36 obtained in Experiment 1 was about 35°–40° C. as shown in FIG. 1 or 2 when incubated in usual manner in 50 mM phosphate buffer (pH 7.0) for 60 min.

Figure 3:
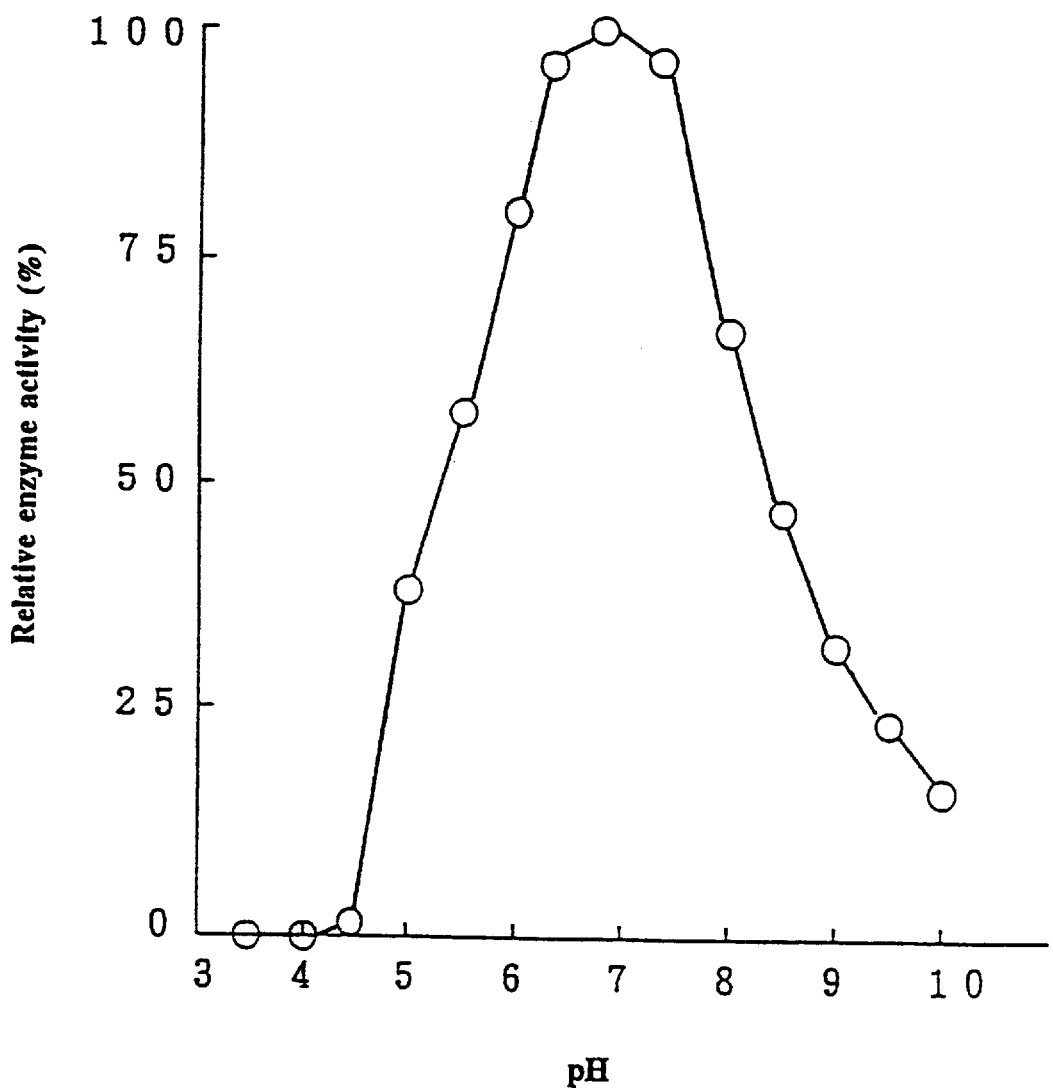
FIG. 3 shows the optimum pH of enzyme M-11.
Figure 4:
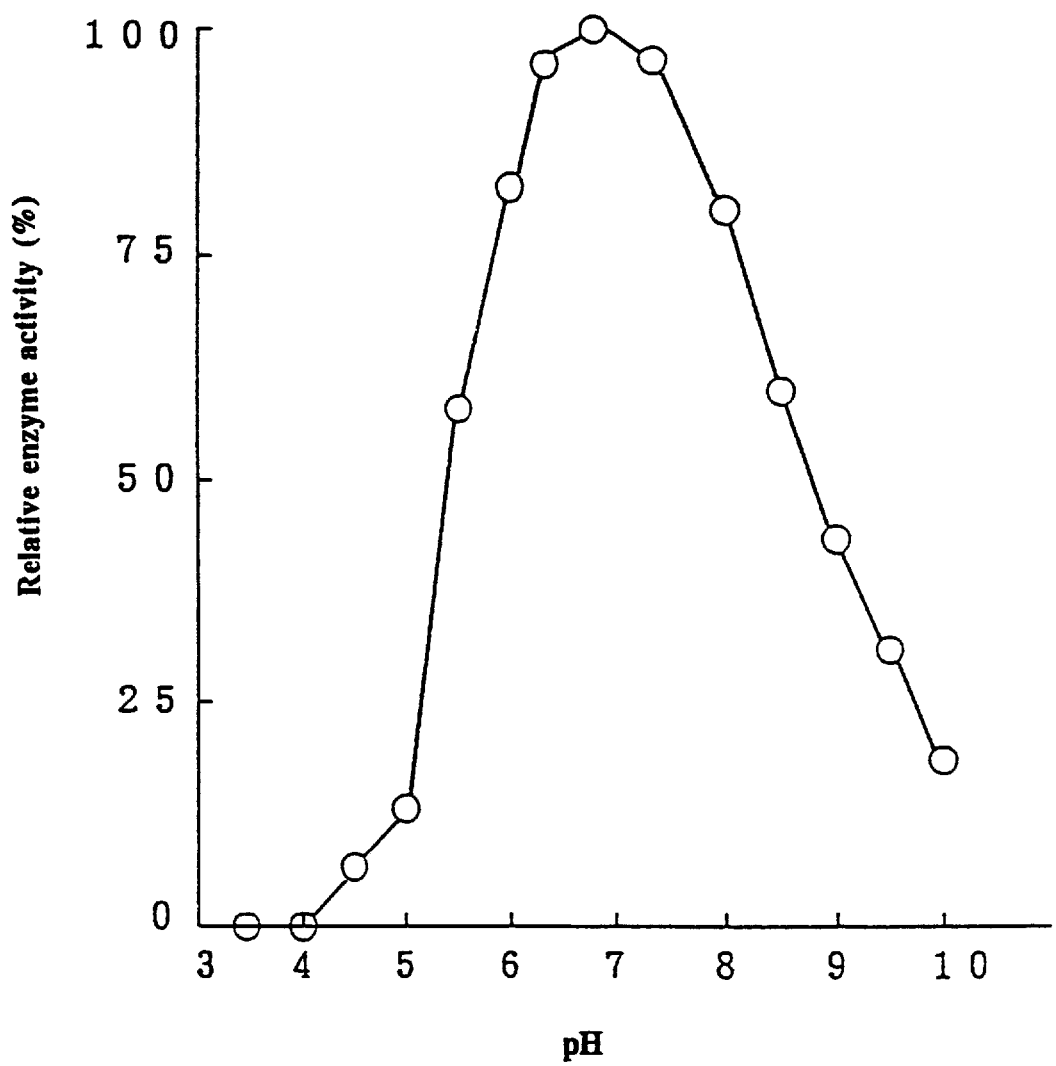
FIG. 4 shows the optimum pH of enzyme Q36.

Experiment 2-5
Optimum PH
The optimum pH of the purified enzymes M-11 and Q36 obtained in Experiment 1 was about 6.4–7.2 as shown in FIG. 3 or 4 when experimented in usual manner by incubating them at 40° C. for 60 min in 50 mM acetate buffer, phosphate buffer or sodium carbonate-sodium hydrogen carbonate buffer having different pHs.

Experiment 2-6
Thermal stability
The purified enzymes M-11 and Q36 obtained in

Figure 5:
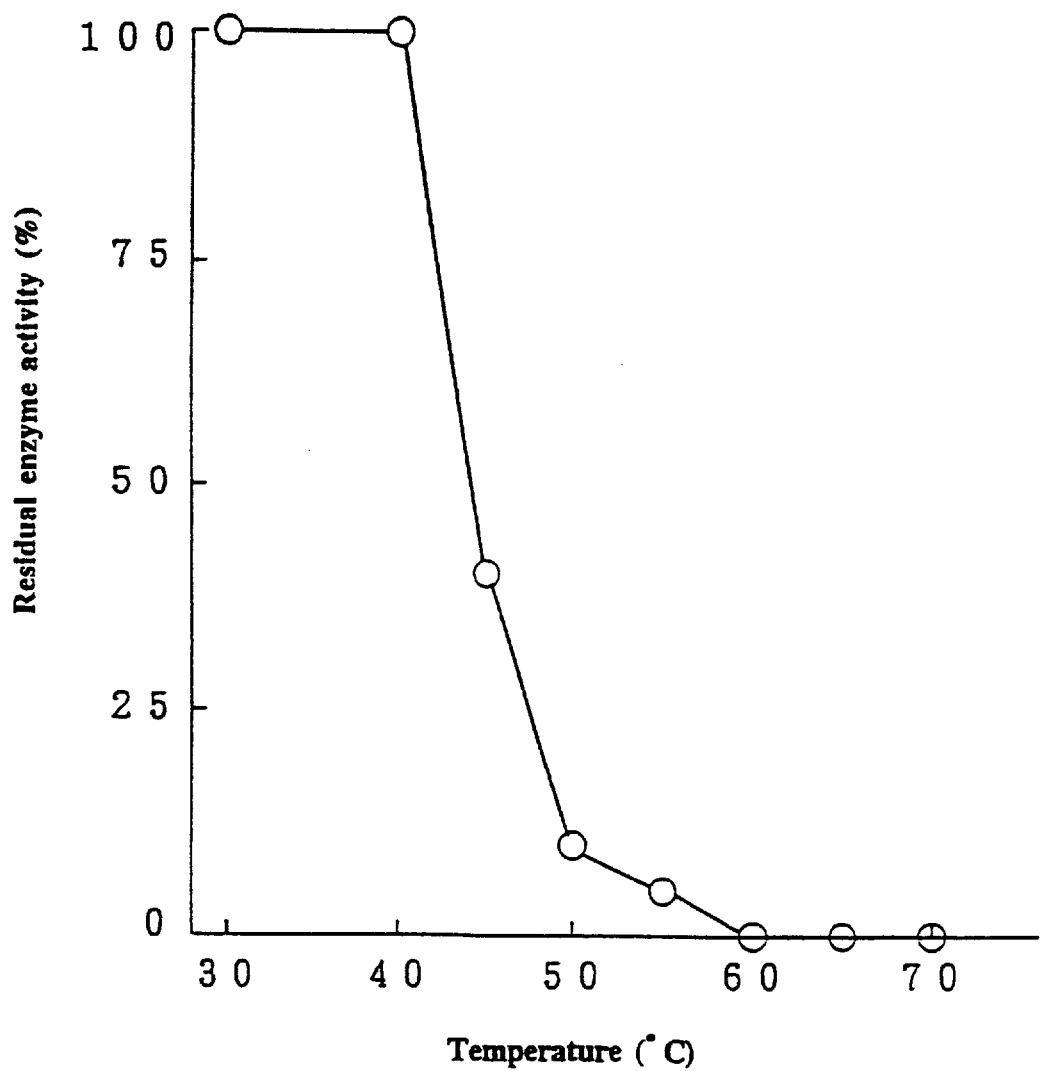
FIG. 5 shows the thermal stability of enzyme M-11.
Figure 6:
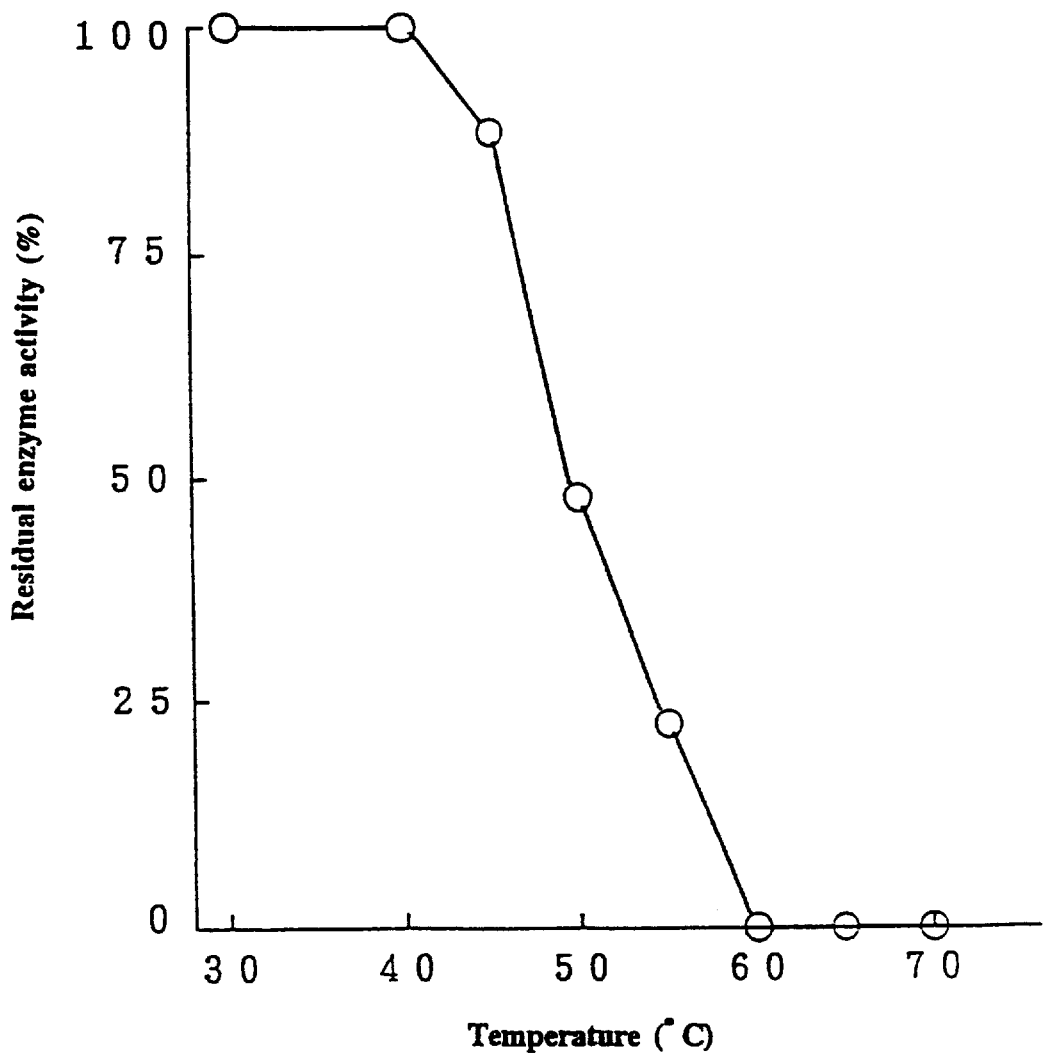
FIG. 6 shows the thermal stability of enzyme Q36.

Experiment 1 were stable up to a temperature of about 35°–40° C. as shown in FIGS. 5 and 6 when experimented in usual manner by incubating them in 50 mM phosphate buffer (pH 7.0) for 60 min.

Figure 7:
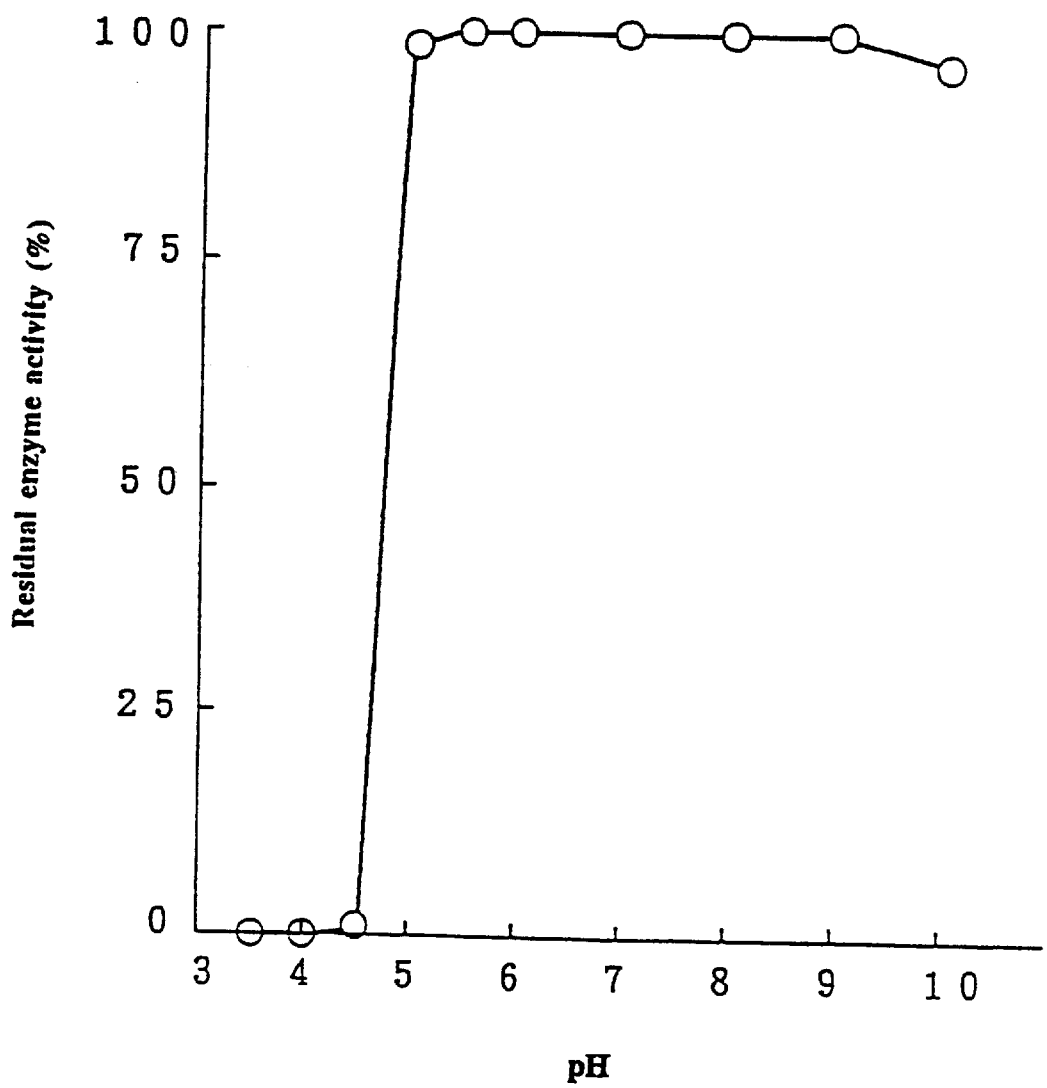
FIG. 7 shows the pH stability of enzyme M-11.
Figure 8:
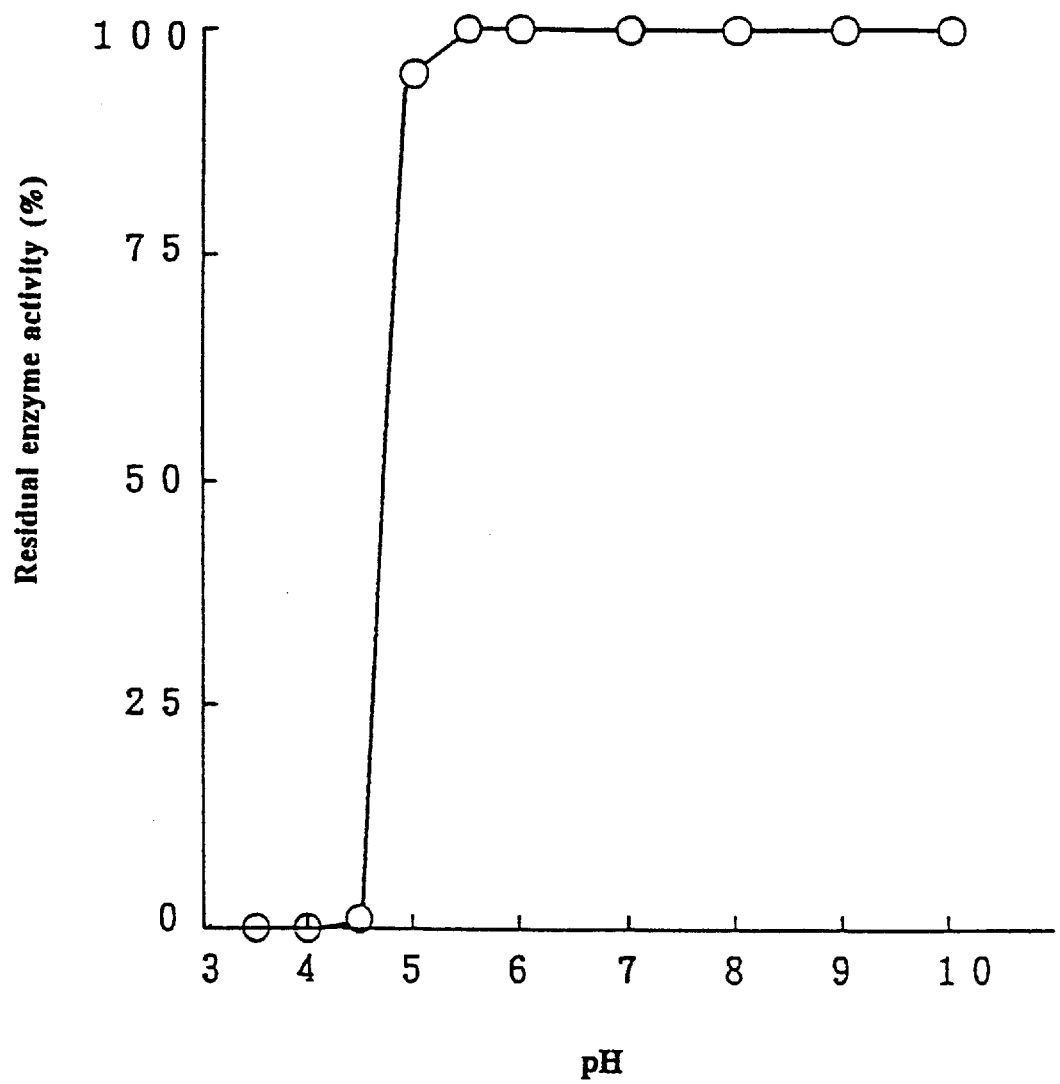
FIG. 8 shows the pH stability of enzyme Q36.

Experiment 2-7
pH Stability
The purified enzymes M-11 and Q36 obtained in Experiment 1 were stable up to a pH of about 5.5–11.0 as shown in FIGS. 7 and 8 when experimented in usual manner by incubating them at 25° C. for 16 hours in 50 mM acetate buffer, phosphate buffer or sodium carbonate-sodium hydrogen carbonate buffer having different pHs.

Experiment 2-8
Amino acid sequence containing the N-terminal
The amino acid sequence containing the N-terminal of the purified enzyme M-11 obtained in Experiment 1 was analyzed on "MODEL 470 A", a gas-phase protein sequencer commercialized by Applied Biosystems, Inc., Foster City, USA, revealing that enzyme M-11 has an amino acid sequence as shown in SEQ ID NO:12.

The amino acid sequence containing the N-terminal of the purified enzyme Q36 was similarly analyzed as in enzyme M-11 revealing that it has an amino acid sequence as shown in SEQ ID NO:13.

Experiment 2-9
Partial amino acid sequence
An adequate amount of the purified enzyme M-11 obtained in Experiment 1-1 was weighed, dialyzed against 10 mM Tris-HCl buffer (pH 9.0) at 4° C. for 18 hours, and admixed with 10 mM Tris-HCl buffer (pH 9.0) to give a concentration of about one mg/ml of the enzyme. About one ml of the resultant solution was placed in a container, admixed with 10 μg lysyl endopeptidase, and incubated at 30° C. for 22 hours to partially hydrolyze the enzyme. The resultant hydrolysate was applied to "CAPCELL-PAK C18", a column for reverse-phase high-performance liquid chromatography commercialized by Shiseido Co., Ltd., Tokyo, Japan, which had been previously equilibrated with 0.1 v/v % trifluoroacetate containing 16 v/v e aqueous acetonitrile, followed by feeding to the column 0.1 v/v % trifluoroacetate at a flow rate of 0.9 ml/min while increasing the concentration of acetonitrile from 16 to 64 v/v % to separatory collect fractions containing a peptide fragment about 28 min or 40 min after the initiation of feeding (the peptide fragments were respectively named "peptide fragment A" and "peptide fragment B"). Fractions containing the peptide fragment A or B were separatory pooled, dried in vacuo, and dissolved in 0.1 v/v % trifluoroacetate containing 50 v/v e aqueous acetonitrile. Similarly as in Experiment 2-8, the peptide fragments A and B were analyzed and revealed to have an amino acid sequence as shown in SEQ ID NO:14 and an amino acid sequence as shown in SEQ ID NO:15.

Similarly as in enzyme M-11, enzyme Q36 obtained in Experiment 1-2 was partially hydrolyzed, and the resultant was fed to "μBONDAPAK C18", a column for reverse-phase high-performance liquid chromatography commercialized by Japan Millipore Ltd., Tokyo, Japan, followed by feeding to the column 0.1 v/v % trifluoroacetate containing aqueous acetonitrile ranging from a concentration of 24 v/v % to 44 v/v % at a flow rate of 0.9 ml/ml. Fractions containing a peptide fragment eluted about 22 min or about 40 min after the initiation of feeding (the fractions were respectively called "peptide fragment C" and "peptide fragment D" hereinafter) were respectively collected, pooled, dried in vacuo, and dissolved in 0.1 v/v e trifluoroacetate containing 50 v/v % aqueous acetonitrile. Analyses of the peptide fragments C and D conducted in a similiar fashion as described above revealed that they have amino acid sequences as shown in SEQ ID NOs:16 and 17, respectively.

No enzyme having these physicochemical properties has been known, and this conclusion is that it is a novel substance. Referring to *Rhizoblum sp.* M-11, it is a microorganism which was isolated from a soil of Okayama-city, Okayama, Japan, deposited on Dec. 24, 1992, in National Institute of Bioscience and Human-Technology Agency of Industrial Science and Technology, Tsukuba, Ibaraki, Japan, and accepted under the accession number of FERM BP-4130, and it has been maintained by the institute. *Arthrobacter sp.* Q36 is a microorganism which was isolated from a soil of Soja-city, Okayama, Japan, deposited on Jun. 3, 1993, in the same institute, and accepted under the accession number of FERM BP-4316, and it has been maintained by the institute. Japanese Patent Application No. 349,216/93 applied by the same applicant discloses the properties and features of the non-reducing saccharide-forming enzyme as well as the detailed bacteriological properties of these microorganisms.

The present inventors energetically screened a chromosomal DNA of *Rhizobium sp.* M-11 by using an oligonucleotide as a probe which had been chemically synthesized based on the partial amino acid sequence of enzyme M-11 as revealed in Experiment 2-9, and found a DNA fragment which consists of 2,316 base pairs having a base sequence as shown in the following SEQ ID NO:1 which initiates from the 5'-terminus. The decoding of the base sequence revealed that the enzyme consists of 772 amino acids as shown in SEQ ID NO:2.

Similarly as in enzyme M-11, a chromosomal DNA of enzyme Q36 was-screened by using an oligonucleotide as a probe which had been chemically synthesized based on a partial amino acid sequence of enzyme Q36, and this yielded a DNA fragment having a base sequence consisting of 2,325 base pairs from the 5'-terminus as shown in SEQ ID NO:3. The base sequence was decoded to reveal that enzyme Q36 consists of 775 amino acids and has a partial amino acid sequence containing the N-terminal as shown in SEQ ID NO:4.

The sequential experimental steps used to reveal the base sequence and amino acid sequence as shown in SEQ ID NOs:1 to 4 are summarized as below:

(1) The enzyme was isolated from a culture of a donor microorganism and highly purified. The purified enzyme was partially hydrolyzed with protease, and the resultant 2 different types of peptide fragments were isolated and determined their amino acid sequences;

(2) Separately, a chromosomal DNA was isolated from a donor microorganism's cell, purified and partially digested by a restriction enzyme to obtain a DNA fragment consisting of about 3,000–7,000 base pairs. The DNA fragment was ligated by DNA ligase to a plasmid vector, which had been previously cut with a restriction enzyme, to obtain a recombinant DNA;

(3) The recombinant DNA was introduced into *Escherichia coli* to obtain transformants, and from which an objective transformant containing a DNA encoding the enzyme was selected by the colony hybridization method using as a probe an oligonucleotide which had been chemically synthesized based on the aforesaid partial amino acid sequence; and (4) The recombinant DNA was obtained from the transformant and annealed with a primer, followed by allowing a DNA polymerase to act on the resultant to extend the primer, and determining the base sequence of the resultant complementary chain DNA by the dideoxy chain termination method. The comparison of an amino acid sequence deduced from the determined base sequence with the aforesaid amino acid sequence confirmed that the base sequence encodes the enzyme.

As is explained above, the enzyme, which forms non-reducing saccharides having trehalose structure as an end unit from reducing amylaceous saccharides having a degree of glucose polymerization of 3 or higher, is an enzyme which was found as a result of the present inventors' long-term research. The enzyme has distinct physicochemical properties from those of other conventional enzymes. The present invention is to produce the enzyme by applying recombinant DNA technology. The recombinant DNA, and its preparation and uses are explained in detail with reference to the examples.

The recombinant enzyme as referred to in the invention means all enzymes which are preparable by recombinant DNA technology and capable of forming non-reducing saccharides having trehalose structure as an end unit from reducing amylaceous saccharides having a degree of glucose polymerization of 3 or higher. Generally, the recombinant enzyme according to the present invention has a revealed amino acid sequence, and, as an example, the amino acid sequence, which initiates from the N-terminal as shown in SEQ ID NO:2 or 4, and homologous ones to it can be mentioned. Variants having amino acid sequences homologous to the one as shown in SEQ ID NO:2 or 4 can be obtained by replacing one or more amino acids in SEQ ID NO:2 or 4 with other amino acids without substantially altering the inherent action of the enzyme. Although even when the same DNA is used and depending on the hosts into which the DNA is introduced, ingredients and components of nutrient culture media for culturing transformants, and their cultivation temperature and pH, modified enzymes may be produced which have amino acid sequences similar to that of SEQ ID NO:2 or 4 as well as having an enzymatic action of the enzyme encoded by the DNA but deleted in one or more amino acids located near the N-terminal of the amino acid sequence as shown in SEQ ID NO:2 or 4 and/or having one or more amino acids newly added after the DNA expression to the N-terminal by the modification of intracellular enzymes of hosts. The recombinant enzyme can be obtained from cultures of transformants containing a specific DNA. Examples of such a transformant used in the invention can be prepared by introducing into hosts a DNA having either the base sequence which initiates from the N-terminal or a homologous base sequence to it or a complementary base sequence to them. Such a base sequence may be prepared by replacing one or more bases thereof without altering the amino acid sequence encoded thereby by using the degeneracy of genetic code. Needless to say, one or more bases in the base sequence, which encodes the enzyme or their variants, can be readily replaced with other bases to allow the DNA to actually express the enzyme production in hosts.

The DNA usable in the present invention includes any one of those derived from natural resources and artificially synthesized ones as long as they have such an aforementioned base sequence. The natural resources for the DNA according to the present invention are, for example, microorganisms of the genera Rhizobium, Arthrobacter, Brevibacterium, Flavobacterium, Micrococcus, Curtobacterium, Mycobacterium and Terrabacter, i.e. *Rhizobium sp.* M-11 (FERM BP-4130), *Arthrobacter sp.* Q36 (FERM BP-4316), *Brevibacterium helovolum* (ATCC 11822), *Flavobacterium aquatile* (IFO 3772), *Micrococcus luteus* (IFO 3064), *Micrococcus roseus* (ATCC 186), *Curtobacterium citreum* (IFO 15231), *Mycobacterium smegmatis* (ATCC 19420) and *Terrabacter tumescens* (IFO 12960) from which genes containing the present DNA can be obtained. The aforementioned microorganisms can be inoculated in nutrient culture media and cultured for about 1–3 days under aerobic conditions, and the resultant cells were collected from the cultures and subjected to ultrasonication or treated with a cell-wall lysis enzyme such as lysozyme or β-glucanase to extract genes containing the present DNA. In this case, a proteolytic enzyme such as protease can be used along with the cell-wall lysis enzyme, and, in the case of treating the cells with an ultrasonic disintegrator, they may be treated in the presence of a surfactant such as sodium dodecyl sulfate (SDS) or may be treated with freezing and thawing. The objective DNA is obtainable by treating the resultant call extract with phenol extraction, alcohol sedimentation, centrifugation, protease treatment and/or ribonuclease treatment used in general in this field. To artificially synthesize the present DNA, it can be chemically synthesized by using the base sequence as shown in SEQ ID NO:1or 3, or can be obtained in a plasmid form by inserting a DNA which encodes the amino acid sequence as shown in SEQ ID NO:2 or 4 into an appropriate self-replicable vector to obtain a recombinant DNA, introducing the recombin ant DNA into an appropriate host to obtain a transformant, culturing the transformant, separating the proliferated cells from the resultant culture, and collecting plasmids containing the DNA from the cells.

Such a recombinant DNA is generally introduced into hosts in a recombinant DNA form. Generally, the recombinant DNA contains the aforesaid DNA and a self-replicable vector, and it can be prepared with a relative easiness by recombinant DNA technology in general when the material DNA is in hand. Examples of such a vector are plasmid vectors such as pBR322, pUC18, Bluescript II SK(+), pUB110, pTZ4, pC194, pHV14, TRp7, TEp7, pBS7, etc. ; and phage vectors such as λgt·λC, λgt·λB, ρ11, φ1, φ105, etc. Among these plasmid- and phage-vectors, pBR322, pUC18, Bluescript II SK(+), λgt·λC and λgt·λB are satisfactorily used when the present DNA needs to be expressed in *Escherichia coli*, while pUB110, pTZ4, pC194, ρ11, φ1 and φ105 are satisfactorily used to express the DNA in microorganisms of the genus Bacillus. The plasmid vectors pHV14, TRp7, TEp7 and pBS7 are advantageously used when the recombinant DNA is allowed to grow in 2 or more hosts.

The methods used to insert the present DNA into such a vector in the invention may be conventional methods in this field. A gene containing the present DNA and a self-replicable vector are first digested by a restriction enzyme and/or ultrasonic disintegrator, then the resultant DNA fragments and vector fragments are ligated. To digest DNAs and vectors, restriction enzymes which specifically act on nucleotides, particularly, type II restriction enzymes, more particularly Sau 3AI, Eco RI, Hind III, Bam HI, Sal I, Xba I, Sac I, Pst I, etc., facilitate the ligation of the DNA fragments and vector fragments. To ligate the DNA fragments with vector fragments, they are annealed if necessary, then subjected to the action of a DNA ligase in vivo or in vitro. The recombinant DNA thus obtained is replicable without substantial limitation by introducing it into appropriate hosts, and culturing the resultant transformants.

The recombinant DNA thus obtained can be introduced into appropriate host microorganisms including *Escherichia coli* and those of the genus Bacillus as well as actinomyces and yeasts. In the case of using *Escherichia coli* as a host, the DNA can be introduced thereinto by culturing the host in the presence of the recombinant DNA and calcium ion, while in the case of using a microorganism of the genus Bacillus as a host the competent cell method and the colony hybridization method can be employed. Desired transformants can be cloned by the colony hybridization method or by culturing a variety of transformants in nutrient culture media containing reducing amylaceous saccharides having a degree of glucose polymerization of 3 or higher, and selecting the objective transformants which form non-reducing amylaceous saccharides having trehalose structure as an end unit from the reducing amylaceous saccharides.

The transformants thus obtained extracellularly produce the objective enzyme when cultured in nutrient culture media. Generally, liquid culture media in general supplemented with carbon sources, nitrogen sources and minerals, and, if necessary, further supplemented with small amounts of amino acids and vitamins can be used in the invention. Examples of the carbon sources are saccharides such as starch, starch hydrolysate, glucose, fructose and sucrose. Examples of the nitrogen sources are organic- and inorganic-substances containing nitrogen such as ammonia, ammonium salts, urea, nitrate, peptone, yeast extract, defatted soy been, corn steep liquor, and beef extract. Cultures containing the objective enzyme can be prepared by inoculating the transformants into nutrient culture media, and incubating them at a temperature of 25°–65° C. and a pH of 2–8 for about 1–6 days under aerobic conditions by aeration and agitation. Such a culture can be used intact as an enzyme agent, and, usually, it may be disrupted prior to use with ultrasonic disintegrator and/or cell-wall lysis enzymes, followed by separating the enzyme from the intact cells and cell debris by filtration and/or centrifugation and purifying the enzyme. The methods to purify the enzyme include conventional ones in general. From cultures intact cells and cell debris are eliminated and subjected to one or more methods such as concentration, salting out, dialysis, separatory sedimentation, gel filtration chromatography, ion-exchange chromatography, hydrophobic chromatography, affinity chromatography, gel electrophoresis and isoelectric point electrophoresis.

As described above, the recombinant enzyme according to the present invention has a specific feature of forming non-reducing saccharides having trehalose structure as an end unit from reducing amylaceous saccharides having a degree of glucose polymerization of 3 or higher. The formed non-reducing saccharides have a satisfactorily mild and high-quality sweetness as well as an adequate viscosity and moisture-retaining ability, and, as a great advantageous feature, they can sweeten food products without fear of causing coloration and deterioration because they do not have a reducing residue within their molecule. By using these features a variety of amylaceous saccharides, which have been put aside because of their reducibilities, can be converted into saccharides having a satisfactory handleability and usefulness but having substantially no or extremely-reduced reducibility.

The conversion method is described in more detail, where reducing starch hydrolysates, which are obtainable by partially hydrolyzing amylaceous saccharides such as starch, amylopectin and amylose by acids and/or amylases, can be usually used as the substrate for the present recombinant enzyme. Such a starch hydrolysate can be obtained by conventional methods generally used in the art, and examples thereof include one or more maltooligosaccharides having a degree of glucose polymerization of 3 or higher such as maltotriose, maltotetraose, maltopentaose, maltohexaose and maltoheptaose. As described in "*Handbook of Amylases and Related Enzymes*", 1st edition, edited by The Amylase Research Society of Japan, published by Pergamon Press plc, Oxford, England (1988), α-amylase, maltotetraose-forming amylase, maltopentaose-forming amylase and maltohexaose-forming amylase are especially useful to prepare the reducing amylaceous saccharides used in the invention, and, the use of any one of these amylases readily yields amylaceous saccharide mixtures rich in reducing amylaceous saccharides having a degree of glucose polymerization of 3 or higher in a considerably-high yield. If necessary, the use of a combination of amylases and starch debranching enzymes such as pullulanase and isoamylase can increase the yield of the reducing amylaceous saccharides used as the substrate for the present recombinant enzyme.

In the conversion method according to the present invention, the present recombinant enzyme is allowed to coexist in an aqueous solution containing one or more of the aforesaid reducing amylaceous saccharides as a substrate, and the solution is then allowed to enzymatically react at a prescribed temperature and pH until a desired amount of the objective reducing amylaceous saccharides is formed. Although the enzymatic reaction proceeds even below a concentration of 0.1 w/v % of a substrate, a higher concentration of 2 w/v %, preferably, 5–50 w/v % of a substrate can be satisfactorily used to apply the present conversion method to an industrial-scale production. The temperature and pH used in the enzymatic reaction are set within the ranges of which do not inactivate the recombinant enzyme and allow the recombinant enzyme to effectively act on substrates, i.e. a temperature up to about 55° C., preferably, a temperature in the range of about 40°–55° C., and a pH of 5–10, preferably, a pH in the range of about 6–8. The amount and reaction time of the present recombinant enzyme are chosen dependently on the enzymatic reaction condition. The enzymatic reaction relatively-highly reduces the reducing power of reducing amylaceous saccharides having a degree of glucose polymerization of 3 or higher, and, in the case of maltopentaose, the reducing powder is lowered to about 7% against the original level.

The reaction mixtures obtained by the present conversion reaction can be used intact, and, usually, they are purified prior to use: Insoluble substances are eliminated from the reaction mixtures by filtration and centrifugation, and the resultant solutions are decolored with an activated charcoal, desalted and purified on ion exchangers, and concentrated into syrupy products. Depending on their use, the syrupy products are dried in vacuo and spray-dried into solid products. In order to obtain products which substantially consist of non-reducing saccharides, the aforesaid syrupy products are subjected to one or more methods such as chromatography using an ion exchanger, activated charcoal and silica gel for saccharide separation, separatory sedimentation using alcohol and/or acetone, membrane filtration, fermentation by yeasts, and removal and decomposition of reducing saccharides by alkalis. The methods to treat a large amount of reaction mixture are, for example, fixed bed- or pseudomoving bed-ion exchange column chromatography as disclosed in Japanese Patent Laid-Open Nos. 23,799/83 and 72,598/83, and such a method produces non-reducing saccharide-rich products in an industrial scale and in a considerably-high yield.

The reducing saccharides thus obtained have a wide applicability to a variety of products which are apt to be readily damaged by the reducibility of saccharide sweeteners: For example, they can be satisfactorily used in food products, cosmetics and pharmaceuticals as a sweetener, taste-improving agent, quality-improving agent, stabilizer, filler, excipient and adjuvant. Since the non-reducing saccharides approximately qualitatively form trehalose upon being acted upon by the enzymatic action of a trehalose-releasing enzyme as disclosed in Japanese Patent Application No. 340,343/93, they can be used as an intermediate for the production of trehalose which could not have been readily prepared.

The following examples explain the present invention in more detail, and the recombinant DNA technologies or techniques employed therein are in themselves conventional ones used in the art, for example, those described by J. Sambruck et al. in "*Molecular Cloning A Laboratory Manual*", 2nd edition, published by Cold Spring Harbor Laboratory Press, USA (1989).

EXAMPLE 1

Preparation of recombinant DNA containing DNA derived from enzyme M-11, and transformant

Example 1-1

Preparation of chromosomal DNA

A seed culture of *Rhizobium sp.* M-11 was inoculated into bacto nutrient broth medium (pH 7.0), and cultured at 27° C. for 24 hours with a rotary shaker. The cells were separated from the resultant culture by centrifugation, suspended in TES buffer (pH 8.0), admixed with 0.05 w/v % lysozyme, and incubated at 37° C. for 30 min. The resultant was freezed at −80° C. for one hour, admixed with TSS buffer (pH 9.0), heated to 60° C., and admixed with a mixture solution of TES buffer and phenol, and the resultant solution was chilled with ice, followed by centrifugally collecting the precipitated crude chromosomal DNA. To the supernatant was added 2 fold volumes of cold ethanol, and the precipitated crude chromosomal DNA was collected, suspended in SSC buffer (pH 7.1), admixed with 7.5 μg ribonuclease and 125 μg protease, and incubated at 37° C. for one hour. Thereafter, a mixture solution of chloroform and isoamyl alcohol was added to the reaction mixture to extract the objective chromosomal DNA, and admixed with cold ethanol, followed by collecting the formed sediment containing the chromosomal DNA. The purified chromosomal DNA thus obtained was dissolved in SSC buffer (pH 7.1) to give a concentration of about one mg/ml, and the solution was freezed at −80° C.

Example 1-2

Preparation of recombinant DNA pBMT7 and transformant BMT7

About one ml of the purified chromosomal DNA obtained in Example 1-1 was placed in a container, admixed with about 35 units of Sau 3AI, a restriction enzyme, and enzymatically reacted at 37° C. for about 20 min to partially digest the chromosomal DNA, followed by recovering a DNA fragment consisting of about 3,000–7,000 base pairs by sucrose density-gradient ultracentrifugation. One μg of Bluescript II SK(+), a plasmid vector, was provided, subjected to the action of Bam HI, a restriction enzyme, to completely digest the plasmid vector, admixed with 10 μg of the DNA fragment and 2 units of T4 DNA ligase, and allowed to stand at 4° C. overnight to ligate the DNA fragment to the vector fragment. To the resultant recombinant DNA was added 30 μl of "*Epicurian Coli* ® XLI-Blue", competent cell commercialized by Toyobo Co., Ltd., Tokyo, Japan, allowed to stand under ice-chilled conditions for 30 min, heated to 42° C., admixed with SOC broth, incubated at 37° C. for one hour to introduce the recombinant DNA into *Escherichia coli*.

The resultant transformant was inoculated into agar plate (pH 7.0) containing 50 μg/ml of 5-bromo-4-chloro-3-indolyl-β-galactoside, and cultured at 37° C. for 18 hours, followed by placing a nylon film on the agar plate to fix thereon about 4,400 colonies formed on the agar plate. Based on the amino acid sequence of Pro-Glu-Trp-Glu-Lys located at positions from 17 to 21 in the amino acid sequence of the peptide fragment A as revealed in Experiment 2-9, the base sequence of probe 1 as shown in SEQ ID NO:5 was chemically synthesized, labelled with $^{32}$P, and hybridized with the colonies of transformants fixed on the nylon film, followed by selecting 9 transformants which exhibited a strong hybridization.

The objective recombinant DNA was selected in usual manner from the 9 transformants, and, in accordance with the method described by E. M. Southern in *Journal of Molecular Biology*, Vol.98, pp.503–517 (1975), hybridized with probe 2 having the base sequence as shown in SEQ ID NO:6 which had been chemically synthesized based on the amino acid sequence of Thr-Glu-Phe-Trp-Asp located at positions from 16 to 20 in the amino acid sequence of the peptide fragment B as revealed in Experiment 2-9, followed by selecting a recombinant DNA which strongly hybridized with probe 2. The recombinant DNA and transformant thus selected were respectively named pBMT7 and BMT7.

Figure 9:
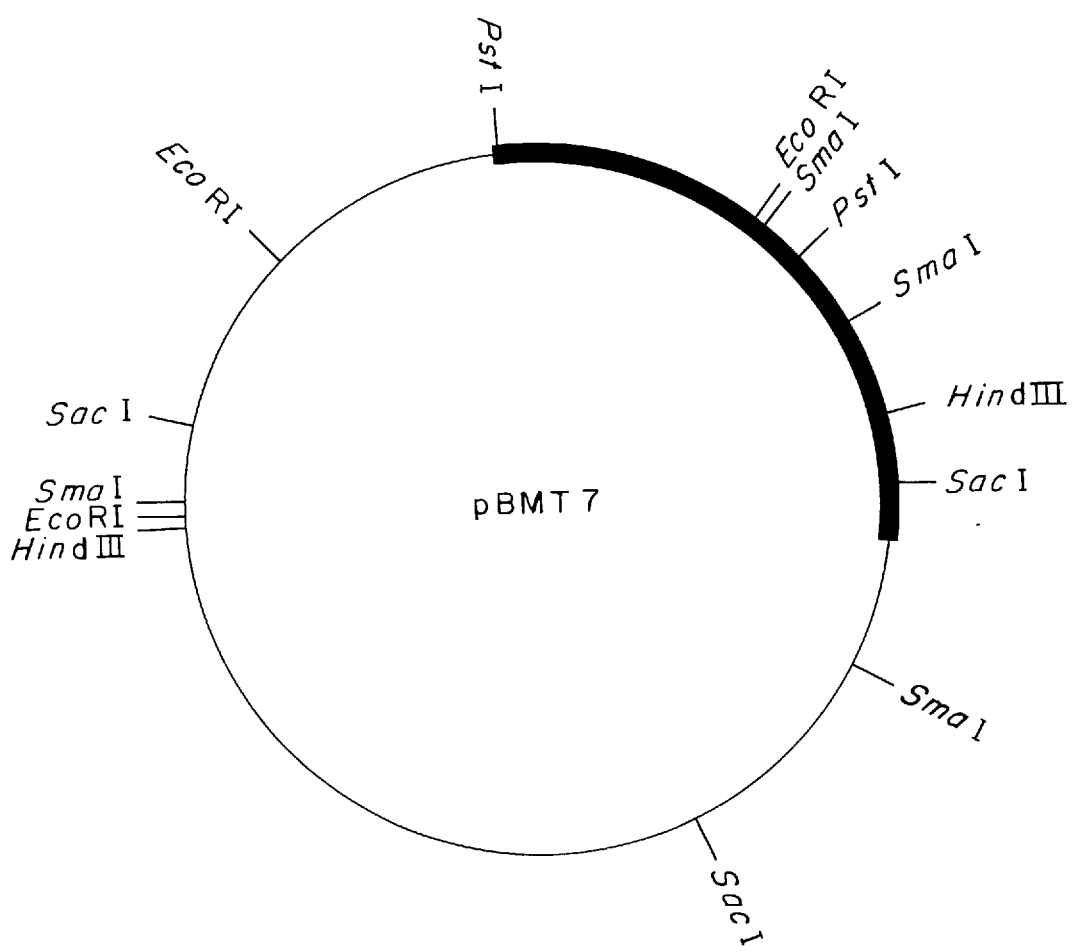
FIG. 9 is a restriction map of the recombinant DNA pBMT7 according to the present invention. In the figure, a bold-line represents a DNA encoding enzyme M-11.

The transformant BMT7 obtained in the above was inoculated into L-broth (pH 7.0) containing 100 μg/ml ampicillin, and cultured at 37° C. for 24 hours with a rotary shaker. After completion of the culture, the cells were collected from the culture by centrifugation, and treated with the alkaline method in general to extracellularly extract a recombinant DNA. The resultant DNA was in usual manner purified and analyzed to find that the recombinant DNA pBMT7 consists of about 9,300 base pairs and has a structure expressed by the restriction map as shown in FIG. 9. It was revealed that as shown in FIG. 9 the DNA consisting of 2,316 base pairs encoding enzyme M-11 is located in the downstream near to the digested site by Pst I, a restriction enzyme.

Example 1-3

Production of enzyme by transformant

A liquid medium consisting of 2.0 w/v % maltose, 0.5 w/v % peptone, 0.1 w/v % yeast extract, 0.1 w/v % disodium hydrogen phosphate and 0.1 w/v % potassium dihydrogen phosphate was adjusted to pH 7.0, admixed with 50 μg/ml ampicillin, autoclaved at 120° C. for 20 min, cooled and inoculated with a seed culture of transformant BMT7 obtained in Example 1-2, followed by culturing the transformant at 37° C. for 24 hours with a rotary shaker. The resultant culture was treated with an ultrasonic disintegrator to disrupt cells, and the resultant suspension was centrifuged to remove insoluble substances. The supernatant thus obtained was assayed for the enzyme activity to find that one L of the culture yielded about 3,000 units of the enzyme.

As a control, a seed culture of *Escherichia coli* XLI-Blue or *Rhizoblum sp.* M-11 was inoculated into a fresh preparation of the same liquid culture medium but free of ampicillin, and, in the case of the culture of *Rhizoblum sp.* M-11, it was cultured and treated similarly as above except that the culturing temperature was set to 30° C. Assaying the resultant activity, one L culture of *Rhizobium sp.* M-11 yielded about 1,500 units of the enzyme, and the yield was significantly lower than that of transformant BMT7. *Escherichia coll* XLI-Blue used as a host did not form the enzyme.

Thereafter, the enzyme produced by the transformant BMT7 and purified similarly as in Experiment 1-1, was examined on its properties and characteristics. As a result, it was revealed that it has substantially the same physicochemical properties as that of Experiment 2 showing a molecular weight of about 76,000–87,000 daltons on SDS-PAGE and an isoelectric point of about 3.6–4.6 on isoelectrophoresis. The results indicate that the present enzyme can be prepared by recombinant DNA technology, and the yield is significantly increased thereby.

EXAMPLE 2

Preparation of complementary DNA derived from enzyme M-11 and determination of its base sequence and amino acid sequence Two μg of the recombinant DNA pBMT7 obtained by the method in Example 1-2 was weighed, admixed with 2M aqueous sodium hydroxide solution to effect degeneration, and admixed with an adequate amount of cold ethanol, followed by collecting the resultant sediment containing a template DNA and drying the sediment in vacuo. To the template DNA were added 50 pmole/ml of a chemically synthesized primer 1 having the base sequence as shown in SEQ ID NO:7, and 10 μl of 40 mM Tris-HCl buffer (pH 7.5) containing 20 mM magnesium chloride and 50 mM sodium chloride, and incubated at 65° C. for 2 min to effect annealing, and the mixture was admixed with 2 μl of an aqueous solution containing dATP, dGTP and dTTP in respective amounts of 7.5 μM, 0.5 μl of [α-$^{32}$P]dCTP (2 mCi/ml), one μl of 0.1M dithiothreitol, and 2 μl of 1.5 units/ml T7 DNA polymerase, followed by incubating the resultant mixture at 25° C. for 5 min to extend the primer 1 from the 5'-terminus to the 3'-terminus. Thus, a complementary chain DNA was formed.

The reaction product containing the complementary chain DNA was divided into quarters, to each of which 2.5 μl of 50 mM aqueous sodium chloride solution containing 80 μM dNTP and 8 μM ddATP, ddCTP, ddGTP or ddTTP was added, and the resultant mixture was incubated at 37° C. for 5 min, followed by suspending the reaction by the addition of 4 μl of 95 v/v % aqueous formamide solution containing 20 mM EDTA, 0.05 w/v % bromophenol blue and 0.05 w/v % xylene cyanol. The reaction mixture was placed in a container, heated in a boiling-water bath for 3 min, placed on a gel containing 6 w/v % polyacrylamide, and electrophoresed by energizing the gel with a constant voltage of about 2,000 volts to separate DNA fragments, followed by fixing the gel in usual manner, drying and subjecting the resultant gel to autoradiography.

Analyses of the DNA fragments separated on the radiogram revealed that the complementary chain DNA contains the base sequence consisting of 2,936 base pairs as shown in SEQ ID NO:10. An amino acid sequence deduced from the base sequence was as shown in SEQ ID NO:10, and it was compared with the amino acid sequence containing the N-terminal and the partial amino acid sequence of enzyme M-11 as shown in SEQ ID NO:12, 14 or 15, and found that the amino acid sequence containing the N-terminal of SEQ ID NO:12 corresponded to the amino acid sequence at positions from 1 to 20 of SEQ ID NO:10, and the partial amino acid sequence of SEQ ID NO:14 or 15 corresponded to the amino acid sequence at positions from 486 to 506 or at positions from 606 to 626 of SEQ ID NO:10. The results indicate that the enzyme produced from *Rhizoblum sp*. M-11 has the amino acid sequence of SEQ ID NO:2, and the enzyme derived from the microorganism is encoded by the DNA having the base sequence as shown in SEQ ID NO:1.

EXAMPLE 3

Preparation of recombinant DNA containing DNA derived from *Arthrobacter sp*. Q36, and transformant Example 3-1
Preparation of chromosomal DNA Similarly as in Example 1-1, a chromosomal DNA was isolated from *Arthrobacter sp*. Q36, purified and dissolved in SSC buffer (pH 7.1) to give a concentration of about one mg/ml, and the resultant solution was freezed at −80° C.

Example 3-2
Preparation of recombinant DNA pBQT13 and transformant BQT13

The purified chromosomal DNA obtained in Example 3-1 was partially digested similarly as in Example 1-2, followed by recovering a DNA fragment consisting of about 3,000–6,000 base pairs by sucrose density gradient ultracentrifugation. The DNA fragment was ligated to a lysate of Bluescript II SK(+) which had been treated with Bam HI similarly as in Example 1-2, and the resultant recombinant DNA was introduced into *Escherichia coli* XLI-Blue. The transformants thus obtained were cultured similarly as in Example 1-2 in an agar plate containing 5-bromo-4-chloro-3-indolyl-β-D-galactoside, and the resultant about 4,500 colonies were fixed on a nylon film, while probe 3 having the base sequence as shown in SEQ ID NO:8 was chemically synthesized based on the amino acid sequence as expressed by Phe-Asp-Val-Asp-Trp-Asp, which are located at positions from 11 to 16 in the amino acid sequence of the peptide fragment D as shown in SEQ ID NO:17, labelled with $^{32}P$, and hybridized with transformant colonies which had been fixed on the nylon film, followed by selecting 8 transformants which strongly hybridized with probe 3.

Similarly as in Example 1-2, the objective recombinant DNA was selected from the 8 transformants, and hybridized with probe 4 having the base sequence as shown in SEQ ID NO:9 which had been chemically synthesized based on the amino acid sequence located at positions from 16 to 20, i.e. Thr-Glu-Phe-Trp-Asp, in SEQ ID NO:16, followed by selecting a recombinant DNA which strongly hybridized with probe 4. The recombinant DNA and transformant thus selected were respectively named pBQT13 and BQT13.

Figure 10:
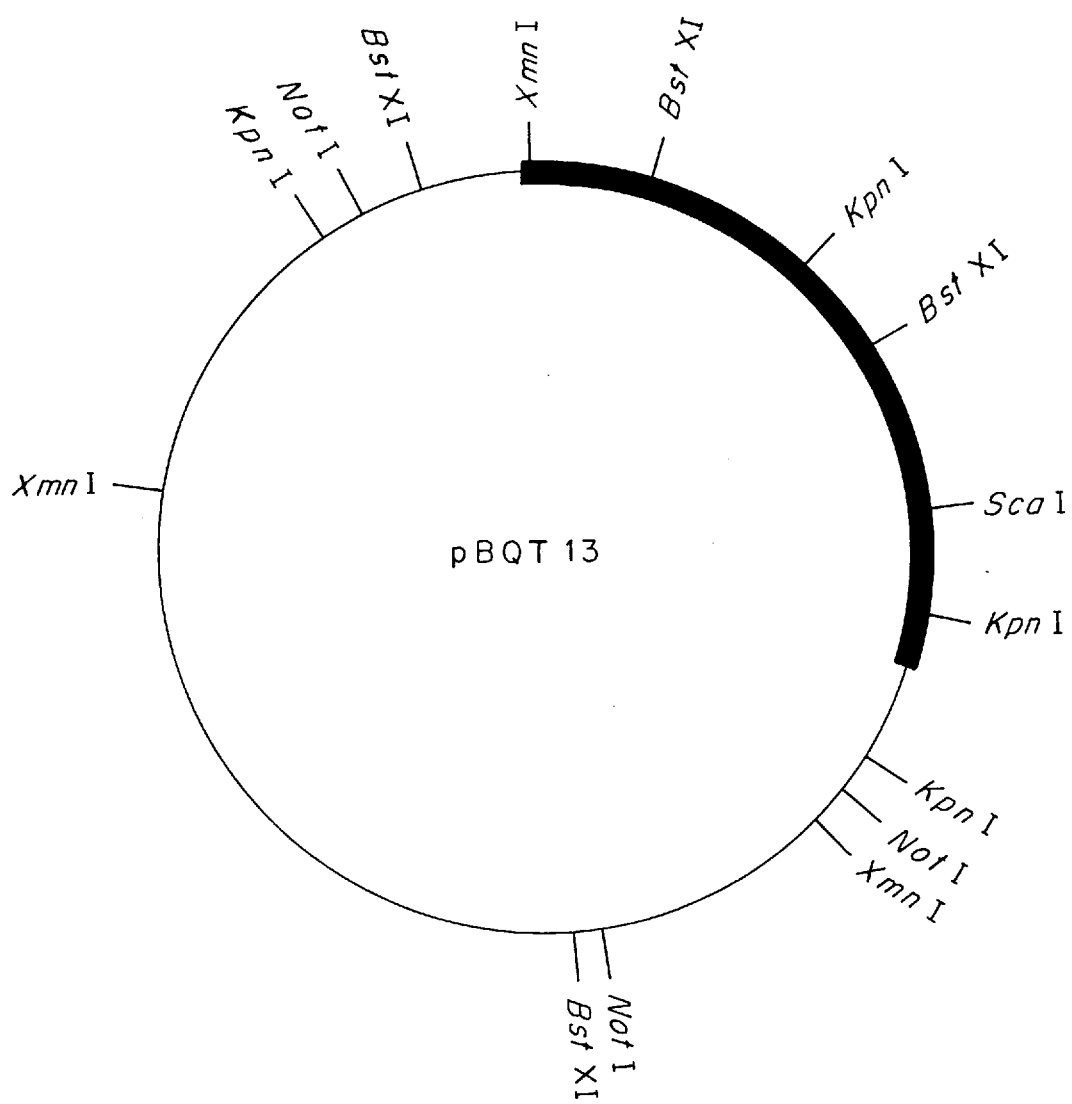
FIG. 10 is a restriction map of the recombinant DNA pBQT13 according to the present invention. In the figure, a bold-line represents a DNA encoding enzyme Q36.

The transformant BQT13 was inoculated into L-broth containing ampicillin, and cultured similarly as in Example 3-2, and the proliferated cells were collected from the resultant culture, and from which a recombinant DNA was extracted, purified and analyzed to reveal that the recombinant pBQT13 consists of about 7,200 base pairs and has a structure expressed by the restriction map as shown in FIG. 10. As shown in FIG. 3, it was reveal that the DNA, which consists of 2,325 base pairs and encodes the DNA of enzyme Q36, is located in the downstream near the cleavage site of Xmn I.

Example 3-3
Production of enzyme by transformant BQT13

A liquid culture medium consisting of 2.0 w/v % maltose, 0.5 w/v % peptone, 0.1 w/v % yeast extract, 0.1 w/v % disodium hydrogen phosphate and 0.1 w/v % potassium dihydrogen phosphate was adjusted to pH 7.0, admixed with 50 μg/ml ampicillin, autoclaved at 120° C. for 20 min, cooled and inoculated with a seed culture of the transformant BQT13 obtained in Example 3-2, followed by culturing the transformant at 37° C. for 24 hours by a rotary shaker. The resultant culture was treated with an ultrasonic disintegrator to disrupt cells, and the resultant suspension was centrifuged to remove insoluble substances. The supernatant thus obtained was assayed for the enzyme activity to find that one L of the culture yielded about 2,450 units of the enzyme.

As a control, *Escherichia coli* XLI-Blue or *Arthrobacter sp*. Q36 was inoculated in a fresh preparation of the same liquid culture medium but free of ampicillin, and cultured and treated similarly as above except that the culturing temperature was set to 30° C. The assay of the activity of the resultants showed that one L of the culture of *Arthrobacter sp*. Q36 yielded about 1,200 units of the enzyme, a level which was significantly lower than that of the transformant BQT13. *Escherichia coli* XLI-Blue used as a host did not form the enzyme.

Thereafter, the enzyme produced by the transformant BMT7 was purified similarly as in Experiment 1-1, and examined on the properties and characteristics. As a result, it was revealed that it has substantially the same physicochemical properties as shown in Experiment 2 of a molecular weight of about 76,000–87,000 daltons on SDS-PAGE and an isoelectric point of about 3.6–4.6 on isoelectrophoresis.

The results indicate that the enzyme can be prepared by recombinant DNA technology, and the yield might be significantly increased thereby.

EXAMPLE 4

Preparation of complementary chain DNA derived from *Arthrobacter sp*. Q36, and determination of its base sequence and amino acid sequence The recombinant DNA pBQT13 obtained in Example 3-2 was similarly treated as in Example 2 to form a template DNA which was then annealed together with the primer 1, followed by allowing T7 DNA polymerase to act on the resultant to extend the primer 1 from the 5'-terminus to 3'-terminus to obtain a complementary chain DNA. Similarly as in Example 2, the complementary chain DNA was subjected to the dideoxy chain terminator method to analyze DNA fragments isolated on a radiogram. The result revealed that the complementary chain DNA contained a base sequence consisting of 3,073 base pairs and an amino acid sequence deduced from the base sequence were as shown in SEQ ID NO:11. The amino acid sequence was compared with respect to the amino acid sequence containing the N-terminal and the partial amino acid sequence of SEQ ID NO:13, 16 or 17, and found that the amino acid sequence containing the N-terminal of SEQ ID NO:13 corresponded to that located at positions from 1 to 20 in SEQ ID NO:11, and the partial amino acid sequence of SEQ ID NO:16 and 17 corresponded to the amino acid sequence located at positions from 606 to 625 or from 110 to 129 in SEQ ID NO:11. The results indicate that enzyme Q36 has the amino acid sequence of SEQ ID NO:4, and it is encoded by the DNA having the base sequence as shown in SEQ ID NO:3.

EXAMPLE 5
Preparation of recombinant enzyme

In 500-ml Erlenmeyer flasks were placed 100 ml aliquots of a liquid culture medium (pH 7.0) consisting of 2.0 w/v % maltose, 0.5 w/v % peptone, 0.1 w/v % yeast extract, 0.1 w/v % disodium hydrogen phosphate and 0.1 w/v % potassium dihydrogen phosphate, and to each flask was added 50 μg/ml ampicillin and autoclaved at 120° C. for 20 min. Thereafter, the flasks were cooled and inoculated with the transformant BMT7 obtained in Example 1-2, followed by culturing the transformant at 27° C. for 24 hours by a rotary shaker. Apart from this, 18 L of a fresh preparation of the same liquid culture medium was placed in an Erlenmeyer flask, admixed with 50 μg/ml ampicillin, sterilized at 120° C. for 20 min, cooled and inoculated with one v/v % of the seed culture obtained in the above, followed by the culture at 37° C. for 24 hours under aeration and agitation conditions. The resultant culture was treated with an ultrasonic disintegrator to disrupt cells, and the resultant suspension was centrifuged to remove insoluble substances. The supernatant thus obtained was assayed for the enzyme activity to show that one L of the culture yielded about 3,000 units of the enzyme. The supernatant was purified by the method in Experiment 1-1 to obtain an about 50 ml aqueous solution containing about 135 units/ml of a recombinant enzyme having a specific activity of about 200 units/mg protein.

EXAMPLE 6
Preparation of recombinant enzyme

Recombinant BQT13 obtained by the method in Example 3-2 was cultured similarly as in Example 5, and the resultant culture was treated with an ultrasonic integrator to disrupt cells. The resultant suspension was centrifuged to remove insoluble substances, and the resultant supernatant was assayed for the enzyme activity to reveal an enzyme production of about 2,450 units per L of the culture. The supernatant was purified by the method in Experiment 1-1 to obtain an approximately 45 ml aqueous solution containing about 120 units/ml of a recombinant enzyme having a specific activity of about 200 units/mg protein.

EXAMPLE 7
Conversion of starch hydrolysate by recombinant enzyme

A potato starch was suspended in water to give a 6 w/w % suspension which was then autoclaved at 120° C. for 10 min to gelatinize the starch. The gelatinized starch was rapidly cooled to 50° C., adjusted to a pH of about 4.5, admixed with 2,500 units/g starch, d.s.b., of an isoamylase specimen commercialized by Hayashibara Biochemical Laboratories, Inc., Okayama, Japan, and enzymatically reacted at 50° C. for 20 hours. The reaction mixture was adjusted to pH 6.0, autoclaved at 120° C. for 10 min to inactivate the remaining enzyme, rapidly cooled to 45° C., admixed with 150 units/g starch, d.s.b., of "TERMAMYL 60L", an α-amylase specimen commercialized by Novo Nordisk Bioindustri A/S, Copenhagen, Denmark, and enzymatically reacted at 45° C. for 24 hours to obtain a reaction mixture containing reducing amylaceous saccharides having a degree of glucose polymerization of 3 or higher such as maltotriose, maltotetraose and maltopentaose. The reaction mixture was autoclaved at 120° C. for 20 min to inactivate the remaining enzyme, rapidly cooled to 45° C., admixed with one unit/g starch, d.s.b., of the recombinant enzyme obtained in Example 5, and enzymatically reacted at 45° C. for 96 hours. The resultant reaction mixture was heated at 96° C. for 10 min to inactivate the remaining enzyme, cooled and filtered, and the resultant filtrate was in usual manner decolored with an activated charcoal, desalted and purified by an ion exchanger and concentrated to obtain an about 70 w/w % syrup, d.s.b., in a yield of about 91%, d.s.b.

Analysis of the syrup conducted by the method of Experiment 2-1 revealed that it had a DE (dextrose equivalent) of 18.7 and contained as a main component, on a dry solid basis, 8.4 w/w % α-glucosyl trehalose, 5.6 w/w % α-maltosyl trehalose, 37.9 w/w % α-maltotriosyl trehalose, and that the greater part of the aforesaid reducing saccharides were converted into their corresponding non-reducing saccharides. The product, having a mild-and moderate sweetness as well as an adequate viscosity and moisture-retaining ability, can be satisfactorily used in food products, cosmetics and pharmaceuticals as a sweetener, taste-improving agent, taste-improving agent, quality-improving agent, stabilizer, filler, excipient and adjuvant. The product contains non-reducing saccharides in a relatively-high content, so it can be also used as an intermediate for preparing trehalose.

EXAMPLE 8
Conversion of starch hydrolysate by recombinant enzyme

Potato starch was suspended in water to give a concentration of 33 w/w %, d.s.b., and the suspension was admixed with 0.1 w/w % calcium carbonate, d.s.b. The resultant suspension was admixed with 0.2 w/w % per g starch, d.s.b., of "TERMAMYL 60L", an α-amylase specimen commercialized by Novo Nordisk Bioindustri A/S, Copenhagen, Denmark, and enzymatically reacted at 95° C. for 15 min. The reaction mixture was autoclaved at 120° C. for 10 min to inactivate the remaining enzyme, rapidly cooled, admixed with 5 units/g starch, d.s.b., of a maltotetraose-forming amylase derived from *Pseudomonas stutzeri* as disclosed in Japanese Patent Laid-Open No. 240,784/88, and enzymatically reacted at 55° C. for 6 hours. Thereafter, the resultant reaction mixture was admixed with 30 units/g starch, d.s.b., of "α-amylase 2A", an α-amylase specimen commercialized by Ueda Chemical Co., Ltd., Osaka, Japan, and enzymatically reacted at 65° C. for 4 hours to form about 50 w/w %, d.s.b., of reducing amylaceous saccharides having a degree of glucose polymerization of 3 or higher such as maltotriose, maltotetraose and maltopentaose. The resultant mixture was autoclaved at 120° C. for 10 min to inactivate the remaining enzyme, rapidly cooled to 45° C., adjusted to pH 6.5, admixed with 2 units/g amylaceous saccharide, d.s.b., of the recombinant enzyme obtained in Example 5, and enzymatically reacted at 45° C. for 64 hours. The reaction mixture thus obtained was heated at 95° C. for 10 min to inactivate the remaining enzyme, cooled, filtered, decolored in usual manner with an activated charcoal, desalted and purified with an ion exchanger, and concentrated to obtain a syrupy product with a concentration of about 70 w/w %, d.s.b., in a yield of about 90% against the material starch, d.s.b.

Analysis of the syrupy product by the method in Experiment 2-1 revealed that it had a DE of 10.5 and contained as a main component 3.8 w/w % α-glucosyl trehalose, 43.8 w/w % α-maltosyl trehalose, and 1.2 w/w % α-maltotriosyl trehalose, d.s.b., and that most of the reducing amylaceous saccharides contained therein were converted into their corresponding non-reducing saccharides. The product, having a mild and moderate sweetness as well as an adequate viscosity and moisture-retaining ability, can be satisfactorily used in food products, cosmetics and pharmaceuticals as a sweetener, taste-improving agent, quality-improving agent, stabilizer, filler, excipient and adjuvant. The product contains non-reducing saccharides in a relatively-high content, so it can be also used as an intermediate for preparing trehalose.

EXAMPLE 9
Conversion of maltopentaose by recombinant enzyme

A high-purity maltopentaose produced by Hayashibara Biochemical Laboratories, Inc., Okayama, Japan, was dissolved in water to give a concentration of 20 w/w %, d.s.b., and the solution was adjusted to pH 6.5, admixed with one unit/g maltopentaose, d.s.b., of a recombinant enzyme obtained by the method in Example 5, and enzymatically reacted at 45° C. for 48 hours. The reaction mixture was heated at 95° C. for 10 min to inactivate the remaining enzyme, cooled, filtered, concentrated and analyzed by the method in Experiment 2-1 to find that about 92 w/w %, d.s.b., of the material maltopentaose was converted into α-maltotriosyl trehalose.

Four jacketed-stainless steel columns, having a diameter of 5.4 cm and a length of 5 m each, were packed to homogeneity with "XT-1016 (Na$^+$-form)", a strong-acid cation exchange resin commercialized by Tokyo Organic Chemical Industries, Ltd., Tokyo, Japan, and cascaded in series to give a total column length of 20 m. The reaction mixture obtained in the above was fed to the columns at a rate of about 5 v/v % against the resin at an inner column temperature of 55° C., and the columns were fed with 55° C. hot water at an SV (space velocity ) of 0.13 to elute saccharide components. Based on the saccharide composition analysis of the eluate, fractions rich in non-reducing saccharides were collected, pooled, concentrated, dried in vacuo and pulverized to obtain a solid product in a yield of about 55%, d.s.b.

Analysis of the solid product by the method in Experiment 2-1 revealed that it had a DE less than about 0.2 and contained 99.0 w/w % α-maltotriosyl trehalose, d.s.b. The product, having a relatively-low hygroscopicity, a significantly-low reducibility as well as a slight sweetness, can be satisfactorily used in food products, cosmetics and pharmaceuticals as a sweetener, taste-improving agent, quality-improving agent, stabilizer, filler, excipient and adjuvant. The product contains non-reducing saccharides in a relatively-high content, so it can be also used as an intermediate for preparing trehalose.

EXAMPLE 10
Conversion of starch hydrolysate by recombinant enzyme

"PINE-DEX #4", a starch hydrolysate produced by Matsutani Chemical Ind., Co., Ltd., Kyoto, Japan, was dissolved in water to give a concentration of 40 w/w %, d.s.b., and the solution was heated-to 45° C., adjusted to pH 6.5, admixed with one unit/g starch hydrolysate, d.s.b., of a recombinant enzyme obtained by the method in Example 5, and enzymatically reacted for 96 hours to obtain a reaction mixture containing non-reducing saccharides having trehalose structure as an end unit. Thereafter, the reaction mixture was heated at 100° C. for 10 min to inactivate the remaining enzyme, concentrated up to a 20 w/w % solution, d.s.b., cooled to 55° C., adjusted to pH 4.5, admixed with 10 units/g saccharide, d.s.b., of "GLUCOZYME", a glucoamylase specimen commercialized by Nagase Biochemicals, Ltd., Kyoto, Japan, and enzymatically reacted for 40 hours. The reaction mixture was heated at 100° C. for 10 min to inactivate the remaining enzyme, cooled, decolored in usual manner with an activated charcoal, desalted and purified with an ion exchanger, and concentrated to obtain an about 60 w/w % syrupy product containing about 29.7 w/w % trehalose, d.s.b.

Similarly as in Example 9 except for using "CG6000 (Na$^+$-form), the syrupy product was fractionated, followed by collecting fractions containing about 90 w/w % trehalose, d.s.b. The fractions were pooled, concentrated into an about 75 w/w % solution which was then transferred to a crystallizer, admixed with about 2 w/w % trehalose hydrate as a seed crystal against saccharides, d.s.b., and crystallized under gentle stirring conditions to obtain a massecuite with a crystallinity of about 45%. The massecuite was sprayed downward from a nozzle, equipped at the upper part of a spraying tower at a pressure of about 150 kg/cm$^2$ while about 85° C. hot air was flowing downward from the upper part of the tower to accumulate a crystalline powder on a belt conveyer provided on the basement of the tower, followed by gradually transferring it out of the tower. Thereafter, the powder was transferred to an aging tower and aged for 10 hours to complete the crystallization and drying while an about 40° C. hot air was blowing to the contents.

The product, having a substantial non-hygroscopicity and a mild and high-quality sweetness, can be satisfactorily used in food products, cosmetics, pharmaceuticals and feeds as a sweetener, taste-improving agent, quality-improving agent, stabilizer, filler, excipient and adjuvant.

EXAMPLE 11
Conversion of starch hydrolysate by recombinant enzyme

Tapioca starch was suspended in water to give a concentration of 34 w/w % and admixed with 0.1 w/w % calcium carbonate. To the suspension was added 0.2 w/w % per g starch, d.s.b., of "TERMAMYL 60L", an α-amylase specimen commercialized by Novo Nordisk Bioindustri A/S, Copenhagen, Denmark, and enzymatically reacted at 95° C. for 15 min to liquefy the starch. The liquefied product was autoclaved at 120° C. for 10 min to inactivate the remaining enzyme, rapidly cooled to 55° C., adjusted to pH 5.2, admixed with 10 units/g starch, d.s.b., of "α-amylase 2A", an α-amylase specimen commercialized by Ueda Chemical Co., Ltd., Osaka, Japan, and 500 units of an isoamylase specimen commercialized by Hayashibara Biochemical Laboratories, Inc., Okayama, Japan, and enzymatically reacted at 55° C. for 20 hours to form a mixture with a DE of about 29, containing about 60 w/w %, d.s.b., of reducing amylaceous saccharides having a degree of glucose polymerization of 3 or higher such as maltotriose, maltotetraose, maltopentaose and maltohexaose. The mixture was autoclaved at 120° C. for 10 min to inactivate the remaining enzyme, rapidly cooled to 45° C., adjusted to pH 6.5, admixed with 2 units/g amylaceous saccharide, d.s.b., of a recombinant enzyme obtained by the method in Example 6, and enzymatically reacted at 45° C. for 64 hours. The reaction mixture thus obtained was heated at 95° C. for 10 min to inactivate the remaining enzyme, cooled, filtered, decolored in usual manner with an activated charcoal, desalted and purified with an ion exchanger, and concentrated to obtain a syrupy product with a concentration of about 70 w/w %, d.s.b., in a yield of about 90% against the material starch, d.s.b.

Analysis of the syrupy product by the method in Experiment 2-1 revealed that it had a DE of 15.8 and contained as a main component 5.8 w/w % α-glucosyl trehalose, 8.5 w/w % α-maltosyl trehalose, 13.1 w/w % α-maltotriosyl trehalose, 18.9 w/w % α-maltotetraosyl trehalose and 3.6 w/w % α-maltopentaosyl trehalose, d.s.b., and that most of the reducing amylaceous saccharides contained therein were converted into their corresponding non-reducing saccharides. The product, having a mild and moderate sweetness as well as an adequate viscosity and moisture-retaining ability, can be satisfactorily used in food products, cosmetics and pharmaceuticals as a sweetener, taste-improving agent, quality-improving agent, stabilizer, filler, excipient and adjuvant. The product contains non-reducing saccharides in a relatively-high content, so it can be also used as an intermediate for preparing trehalose.

EXAMPLE 12

Conversion of starch hydrolysate by recombinant enzyme

Similarly as in Example 8, a liquefied potato starch was successively subjected to the action of maltotetraose-forming amylase and α-amylase to form a mixture containing about 50 w/w %, d.s.b, of reducing amylaceous saccharides having a degree of glucose polymerization of 3 or higher such as maltotriose, maltotetraose and maltopentaose. The reaction mixture was autoclaved at 120° C. for 10 min to inactivate the remaining enzyme, rapidly cooled to 45° C., adjusted to pH 6.5, admixed with 2 units/g amylaceous saccharide, d.s.b., of a recombinant enzyme obtained by the method in Example 6, and enzymatically reacted at 45° C. for 64 hours. The reaction mixture thus obtained was heated at 95° C. for 10 min to inactivate the remaining enzyme, cooled and filtered, and the filtrate was decolored in usual manner with an activated charcoal, desalted and purified with an ion exchanger, and concentrated to obtain an about 70 w/w % syrupy product in a yield of about 90 w/w % against the material starch, d.s.b.

Analysis of the syrupy product by the method in Experiment 2-1 revealed that it had a DE of 10.3 and contained as a main component 3.6 w/w % α-glucosyl trehalose, 44.0 w/w % α-maltosyl trehalose and 1.0 w/w % α-maltotriosyl trehalose, d.s.b., and that most of the reducing amylaceous saccharides contained in the syrupy product were converted into their corresponding non-reducing saccharides. The product, having a mild and moderate sweetness as well as an adequate viscosity and moisture-retaining ability, can be satisfactorily used in food products, cosmetics and pharmaceuticals as a sweetener, taste-improving agent, quality-improving agent, stabilizer, filler, excipient and adjuvant. The product contains non-reducing saccharides in a relatively-high content, so it can be also used as an intermediate for preparing trehalose.

As is described above, the present invention is based on the finding of a novel enzyme which forms non-reducing saccharides having a trehalose structure as an end unit from reducing saccharides having a degree of glucose polymerization of 3 or higher. The present invention is to explore a way to produce such enzyme by recombinant DNA technology in a relatively-large scale and in a considerably-high yield. The conversion method using the present recombinant enzyme effectively converts reducing amylaceous saccharides into their corresponding non-reducing saccharides which have a mild and high-quality sweetness and an adequate viscosity and moisture-retaining ability, do not have a reducing residue within the molecules, and can sweeten food products without fear of causing an unsatisfactory coloration and deterioration. In addition, the present recombinant enzyme has its amino acid sequence completely, and because of this determined it can be used for the preparation of trehalose and non-reducing saccharides having trehalose structure as an end unit which are premised on being used in food products without fear of causing side effects.

Thus, the present invention is a significant invention which exerts the aforesaid outstanding action and effect as well as giving a great contribution to the field.

While there has been described what is at present considered to be the preferred embodiments of the invention, it will be understood the various modifications may be made therein, and it is intended to cover in the appended claims all such modifications as fall within the true spirits and scope of the invention.

We claim:

1. A method for converting a reducing amylaceous saccharide, comprising the steps of:

transforming a host microorganism with a recombinant DNA molecule encoding an enzyme which forms a non-reducing saccharide having a trehalose structure as an end unit from a reducing amylaceous saccharide having a degree of glucose polymerization of 3 or higher to obtain a recombinant microorganism, wherein the recombinant DNA molecule comprises a nucleotide sequence selected from the group consisting of SEQ ID NO:1, SEQ ID NO:3, SEQ ID NO:10, and SEQ ID NO:11;

culturing the recombinant microorganism to express and produce the enzyme;

recovering the produced enzyme; and subjecting a reducing amylaceous saccharide having a degree of glucose polymerization of 3 or higher to the action of the recovered enzyme to convert the reducing amylaceous saccharide and form a non-reducing saccharide having a trehalose structure as an end unit.

2. The method as claimed in claim 1, wherein said encoded enzyme has the following physicochemical properties:

(1) Molecular weight
About 76,000–87,000 daltons on sodium dodecyl sulfate polyacrylamide gel electrophoresis (SDS-PAGE); and (2) Isoelectric point (pI)
About 3.6–4.6 on isoelectrophoresis.

3. The method as claimed in claim 1, wherein said reducing amylaceous saccharide is selected from the group consisting of starch hydrolysate and an amylaceous substance which has been treated with acid together with or without amylase.

4. The method as claimed in claim 1, wherein said reducing amylaceous saccharide is selected from the group consisting of maltotriose, maltotetraose, maltopentaose, maltohexaose, maltoheptaose, and mixtures thereof.

5. The method as claimed in claim 1, wherein said reducing amylaceous saccharide is a solution of said reducing amylaceous saccharide with a concentration of 50 w/v % or lower, and the subjecting step is carried out at a temperature of 40°–55° C. and a pH of 5–10.

6. The method as claimed in claim 1, wherein said non-reducing saccharide is selected from the group consisting of α-glucosyl trehalose, α-maltosyl trehalose, α-maltotriosyl trehalose, α-maltotetraosyl trehalose, α-maltopentaosyl trehalose, and mixtures thereof.

7. A method for converting a reducing amylaceous saccharide, comprising the steps of:

transforming a host microorganism with a recombinant DNA molecule encoding an enzyme having an activity which forms a non-reducing saccharide having a trehalose structure as an end unit from a reducing amylaceous saccharide having a degree of glucose polymerization of 3 or higher to obtain a recombinant microorganism, wherein the recombinant DNA molecule comprises a nucleotide sequence encoding a variant of an enzyme having the sequence of SEQ ID NO:2 or SEQ ID NO:4 not derived from a microorganism selected from the group consisting of Brevibacterium, Flavobacterium, Micrococcus, Curtobacterium, Mycobacterium and Terrabacter where the variant enzyme has one or more amino acid residues in SEQ ID NO:2 or SEQ ID NO:4 replaced with different amino acids or one or more amino acids deleted from or added to the N-terminus of SEQ ID NO:2 or SEQ ID NO:4 while having substantially the same activity as the enzyme having the sequence of SEQ ID NO:2 or SEQ ID NO:4;

culturing the recombinant microorganism to express and produce the enzyme;

recovering the produced enzyme; and subjecting a reducing amylaceous saccharide having a degree of glucose polymerization of 3 or higher to the action of the recovered enzyme to convert the reducing amylaceous saccharide and form a non-reducing saccharide having a trehalose structure as an end unit.

8. The method according to claim 7, wherein the encoded variant enzyme has the following physicochemical properties:

(1) Molecular weight
   About 76,000–87,000 daltons on sodium dodecyl sulfate polyacrylamide gel electrophoresis (SDS-PAGE); and
(2) isoelectric point (pI)
   About 3.6–4.6 on isoelectrophoresis.

9. The method according to claim 7, wherein the reducing amylaceous saccharide is selected from the group consisting of starch hydrolysate and an amylaceous substance which has been treated with an acid in combination with or without amylase.

10. The method according to claim 7, wherein the reducing amylaceous saccharide is selected from the group consisting of maltotriose, maltotetraose, maltopentaose, maltohexaose, maltoheptaose, and mixtures thereof.

11. The method according to claim 7, wherein the non-reducing saccharide is selected from the group consisting of α-glucosyl trehalose α-maltosyl trehalose, α-maltotriosyl trehalose, α-maltotetraosyl trehalose, α-maltopentaosyl trehalose, and mixtures thereof.

12. The method according to claim 7, wherein the reducing amylaceous saccharide is a solution of said reducing amylaceous saccharide with a concentration of 50 w/v % or lower, and the subjecting step is carried out at a temperature in a range of 40°–55° C. and a pH in a range of 5–10.

\* \* \* \* \*